(12) United States Patent
Cazenave

(10) Patent No.: US 10,653,539 B2
(45) Date of Patent: *May 19, 2020

(54) ELECTROMAGNETIC ACTUATION MECHANISM FOR INDIVIDUAL DIGIT CONTROL OF AN ARTIFICIAL HAND

(71) Applicant: Blain Joseph Cazenave, Vacherie, LA (US)

(72) Inventor: Blain Joseph Cazenave, Vacherie, LA (US)

(*) Notice: Subject to any disclaimer, the term of this patent is extended or adjusted under 35 U.S.C. 154(b) by 154 days.

This patent is subject to a terminal disclaimer.

(21) Appl. No.: 15/848,001

(22) Filed: Dec. 20, 2017

(65) Prior Publication Data

US 2018/0110631 A1    Apr. 26, 2018

Related U.S. Application Data

(63) Continuation of application No. 15/166,387, filed on May 27, 2016, now Pat. No. 9,974,667.

(51) Int. Cl.
| | |
|---|---|
| *A61F 2/70* | (2006.01) |
| *A61F 2/58* | (2006.01) |
| *A61F 2/68* | (2006.01) |
| *A61F 2/50* | (2006.01) |

(52) U.S. Cl.
CPC ............... *A61F 2/70* (2013.01); *A61F 2/583* (2013.01); *A61F 2/68* (2013.01); *A61F 2/586* (2013.01); *A61F 2002/5003* (2013.01); *A61F 2002/5072* (2013.01); *A61F 2002/5073* (2013.01); *A61F 2002/5087* (2013.01); *A61F 2002/5093* (2013.01); *A61F 2002/587* (2013.01); *A61F 2002/6836* (2013.01); *A61F 2002/6845* (2013.01); *A61F 2002/6854* (2013.01); *A61F 2002/6863* (2013.01); *A61F 2002/701* (2013.01)

(58) Field of Classification Search
CPC ...... A61F 2002/6836; A61F 2002/6845; A61F 2002/6863; A61F 2002/701; A61F 2002/741; A61F 2/72; B25J 15/0009
See application file for complete search history.

(56) References Cited

U.S. PATENT DOCUMENTS

| | | | | |
|---|---|---|---|---|
| 2009/0110533 A1* | 4/2009 | Jinno | ...................... | A61B 34/70 414/783 |
| 2012/0150323 A1* | 6/2012 | Wisse | ...................... | A61F 2/588 623/64 |

OTHER PUBLICATIONS

Rutkin, Aviva. Bionic arm gives cyborg drummer superhuman skills. New Scientist. (Year: 2014).*

* cited by examiner

*Primary Examiner* — Christie L Bahena
(74) *Attorney, Agent, or Firm* — Russel O. Primeaux; Jessica C. Engler; Kean Miller LLP

(57) ABSTRACT

The disclosed invention is an innovative, cost-efficient driving mechanism for the prosthetic hand industry that makes the use of only one motor to individually control each digit on a prosthetic hand separately. The use of the novel electromagnetic actuation system, locking mechanism, and spline nut and shaft configuration coupled with the single motor greatly reduces the weight, size and power usage of the prosthetic, increases functionality, minimizes noise, increases and speeds and forces, and orients the parts of the device in a manner that creates an aesthetically appealing design.

23 Claims, 19 Drawing Sheets

ELECTROMAGNETIC ACTUATION MECHANISM FOR INDIVIDUAL DIGIT CONTROL OF AN ARTIFICIAL HAND

This application claims the benefit of U.S. Provisional Patent Application No. 62/167,511 filed on May 28, 2015 and U.S. patent application Ser. No. 15/166,387 filed on May 27, 2016. The disclosures of the referenced application are hereby incorporated herein in its entirety by reference.

The present invention relates to the field of developing individualized exercise training programs, particularly the use of the invention to create polarized training to increase athletic performance.

BACKGROUND OF THE INVENTION

The need for and use of prosthetic hands has been around for centuries. Even today with advancing technologies, the use of the inefficient prosthetic devices is critical as several thousands of people in the United States alone have entire arm amputations and partial/complete hand amputations. After the loss of a limb, a significant part of a patient's recovery and resumption of daily activities is dependent upon the use of a prosthetic device. This recovery becomes more complex when the loss is of an entire hand. In the last twenty years, the prosthetics design and technology has seen major improvements, allowing for more functionality and increased dexterity for upper limp amputees. However, still, there are major needs that can be addressed to further the advancement of prosthetic hand designs to allow prosthetic hand users to have capabilities similar to those of an innate human hand.

Despite attempts to mimic the natural mechanisms of the hand, existing hand models lack dexterity and functionality and are underactuated, bulky, and expensive. The current art does not focus on these shortcomings of the prosthetic itself, but rather on improving the technology used to control prosthetic hand devices. This involves applications that are centered on Brain Computer Interfaces (BCI), signal processing, and feedback control mechanisms. These applications create an interface between the amputee and the prosthetic device and allow users to apply various forces and different grasps that are needed in everyday activities via electromyography technology. These "myoelectric" prosthetic hands use sensors strategically placed on the residual limb to detect muscle contractions that translate into finger movements of the hand. Myoelectric designs that are currently on the market and are reflective of the current state of the art include the Vincent Hand by Vincent Systems, i-Limb Hand by Touch Bionics, i-Limb Pulse by Touch Bionics, BeBionic Hand by RSL Steeper, BeBionic Hand v2 by RSL Steeper, and the Michelangelo Hand by Otto Bock. However, more traditional body powered devices are more accepted than the newer myoelectric designs due to major technology gaps that exist to make these "myoelectric" hands more efficient and feasible for amputees to use.

Problems in the current art with current models include: (1) the weight of the prosthetic device; (2) the cosmetic appearance of the prosthetic; (3) the grasping forces and speeds presently in the art; (4) needed noise reduction; and (5) increased functionality. These "technology gaps" exist due to the difficulty of creating an artificial hand that closely mimics the innate abilities of the natural human hand while keeping the design parameters within reasonable confines of the hand's relative anatomical features (e.g., weight, size, and cosmetic appearance). Addressing all of the needs is challenging and can be generalized by improving the overall driving mechanism of the prosthetic device since the driving mechanism does encompass issues related to device weight, force, speed, noise, and overall functionality.

The driving mechanism of prosthetic hands manipulates the digits of the hand, individually or together, to allow the user to undertake various activities. Several deficiencies of currently available artificial hands relate to the driving mechanisms of these devices, so improving on the design of the mechanism can address these needs and can allow for greater manipulation and dexterity of the prosthetic device by the end user. Several driving mechanisms are currently used to operate prosthetic designs, and each uses a different technique to provide motion to the digits of the prosthetic device. These mechanisms can be classified into one of six categories: (1) body-driven; (2) pneumatic; (3) hydraulic; (4) cable transmission; (5) multiple transmissions; and (6) hybrid combinations.

Body-driven prosthetic devices for upper limb amputees consists of a body harness connected to a cable that leads to the end of the device where the cable is than usually connected to a 2 digit pinching mechanism. The apparatus can be opened or closed by moving the opposing shoulder unto which the harness is fastened. They are cheap, lightweight, durable, and easily assembled, but they have limited grasping capabilities, are awkward in appearance, and constrict the body when in use.

Pneumatic driving mechanisms use a fluid actuator element to provide motion to the digits of a prosthetic hand. These actuator elements contain several parts including a feed channel, fluid pump, and an air chamber that is connected to the movable joints of a prosthetic hand. When the elements are inflated with air, the volume of the elements expands and causes movement of the finger. Pneumatic designs are capable of being small and lightweight with comparable grasping forces to a human hand, but they require large amounts of power to operate and produce loud hissing sounds when in operation.

The hydraulic mechanism has the same advantages of the pneumatic mechanism with added qualities. The hydraulic mechanism uses fluid actuators, but it also contains a multi-valve micro pump with an attached fluid reservoir that allows fluid to be transferred to several elements to move several fingers at the same time. Movement is basically the same in both mechanisms with movement of device caused by the expansion of several actuator elements. The hydraulic mechanism has a lower energy consumption and greater grasping forces than the pneumatic design without the hissing sounds from the actuators. The mechanism has dual functions and can be operated with air or liquid, but weight issues and the potential of hydraulic fluids leaking from the elements causing detrimental damage to the electronic controls is too risky.

Cable transmission mechanisms consist of a combination of cables and pulleys located in the joints of the artificial fingers of the prosthetic hand. The pulleys are operated by servomotors that can turn the pulleys allowing movement of the fingers. These mechanisms are also considered to be lightweight and small with similar grasping forces compared to the hydraulic designs but have limited ability and maintenance issues due to the number of moving parts.

The multiple transmission mechanism is a hybrid mechanism that uses various approaches to provide motion to the fingers of the prosthetic device, and many driving mechanisms fall under this category. However, each mechanism contains but is not limited to a motor and actuator system that is linked to a gearbox which in turn rotates a driveshaft. They work in a manner similar to the cable transmission design but include a blocking system that locks pulleys in place to allow for a position to be held. This design allows for multiple pulleys to be operated by one motor, which can reduce the weight of the hand, but it also reduces the grasping force of the hand since each finger is coupled to the same motor.

The hybrid option is a mixture between the body-powered prosthesis and the externally powered driving mechanism. The most common combination is the use of a body-powered elbow with an electric hand or wrist or an electric elbow with a body-powered hand.

Each mechanism has its advantages and disadvantages depending on the individual user and the intended use of the device. Yet, major technology gaps exist that prevent a more efficient and complete mechanism to be implemented into a prosthetic hand to allow for individual manipulation of all 5 digits including automated thumb rotation. The new technology disclosed herein is an electromagnetic driving mechanism for a prosthetic hand device that fills the current technology gaps in the prosthetic hand industry.

SUMMARY OF THE INVENTION

The disclosed invention is an innovative, cost-efficient driving mechanism for the prosthetic hand industry which makes use of only one motor to individually control each digit on the prosthetic hand separately. The prosthetic hand apparatus is comprised of an artificial hand configuration comprising at least two individual fingers, a single motor, a magnetic actuation system, locking mechanism, and a spline nut and shaft configuration. For the hand apparatus, all individual digits are each spring loaded and each has its own separate ratchet and pawl pair mechanism. The ratchet gears are on the main shaft as with the spline shaft and spline nut configuration, and the pawls are located on the secondary shaft, parallel to the main shaft, driven by the main drive belt in a directional manner due to the implementation of a one-way bearing on the pawl shaft. During operation of the apparatus, the drive spline shaft spins with the ratchet gears engaged by the electromagnetics of the magnetic actuating system, causing the pawl to ratchet on top of the ratchet gear until the shaft stops spinning. Once static, the pawl is engaged into one of the teeth of the gear, causing it to "lock" in place for a grasp to be "held." The digits then can gracefully be released to the "open" position through the use of a dampening spring after the motor is reversed one iteration to release the pawls. In an additional embodiment, the digits can be digitized using an electronic control scheme to gradually release and stop the digits by engaging and disengaging the electromagnetics as needed until the desired digit positions are achieved. If all fingers or one finger is engaged by the mechanism, the motor can be reversed to bring the digits back to the open position. In an additional embodiment, an additional motor is included in the device to control thumb rotation.

In an additional embodiment, an electromagnetic rotary solenoid clutch ("ERSC") with a ratchet gear can be used as part of the magnetic actuation. This design is constructed using a combination of a rotary solenoid and an electromagnetic clutch. The unique clutch design allows for a splined nut attached to the spline shaft to rotate inside of the clutch's hollow magnetic steel core while having the ability to be driven axially via the use of an electromagnetic force. This axial motion drives the plunger assembly of the ERSC with the rubber washer into the ratchet gear, causing the gear to spin with the plunger assembly. The energy from the plunger is transferred to the gear via a friction drive. The use of a friction drive transmission, which has not previously be utilized in prosthetic hands, allows for slippage to occur between the two contacting surfaces when loads above the mechanism's dynamic threshold are grasped.

The features and advantages of this design described in this application can be utilized by a number of different industries such as the automotive and automation fields. In an additional embodiment, this hand could be used in robotics applications in which the flexion and dexterity of a human hand is needed.

BRIEF DESCRIPTION OF THE DRAWINGS

FIG. 1 contains the mechanism platform 22, with the components of the disclosed locking mechanism and the belt drivetrain, using a spline shaft 8 and spline nut assembly 36 with friction surface and thrust bearing. This novel embodiment uses a ratchet and gear pulley system with the spline shaft 8 and spline nut assembly 36 and electromagnets to provide individual digit flexion.

FIG. 10 depicts the apparatus comprising the powertrain/thumb mechanism, the locking mechanism, the belt drivetrain, and the electromagnetic rotary solenoid clutch assembly 10. This embodiment further comprises a shaft coupling 18, a gear box 19, the pawl train, a thrust bearing 30, and an electromagnetic clutch 38.

DETAILED DESCRIPTION OF THE INVENTION

Figure 1:
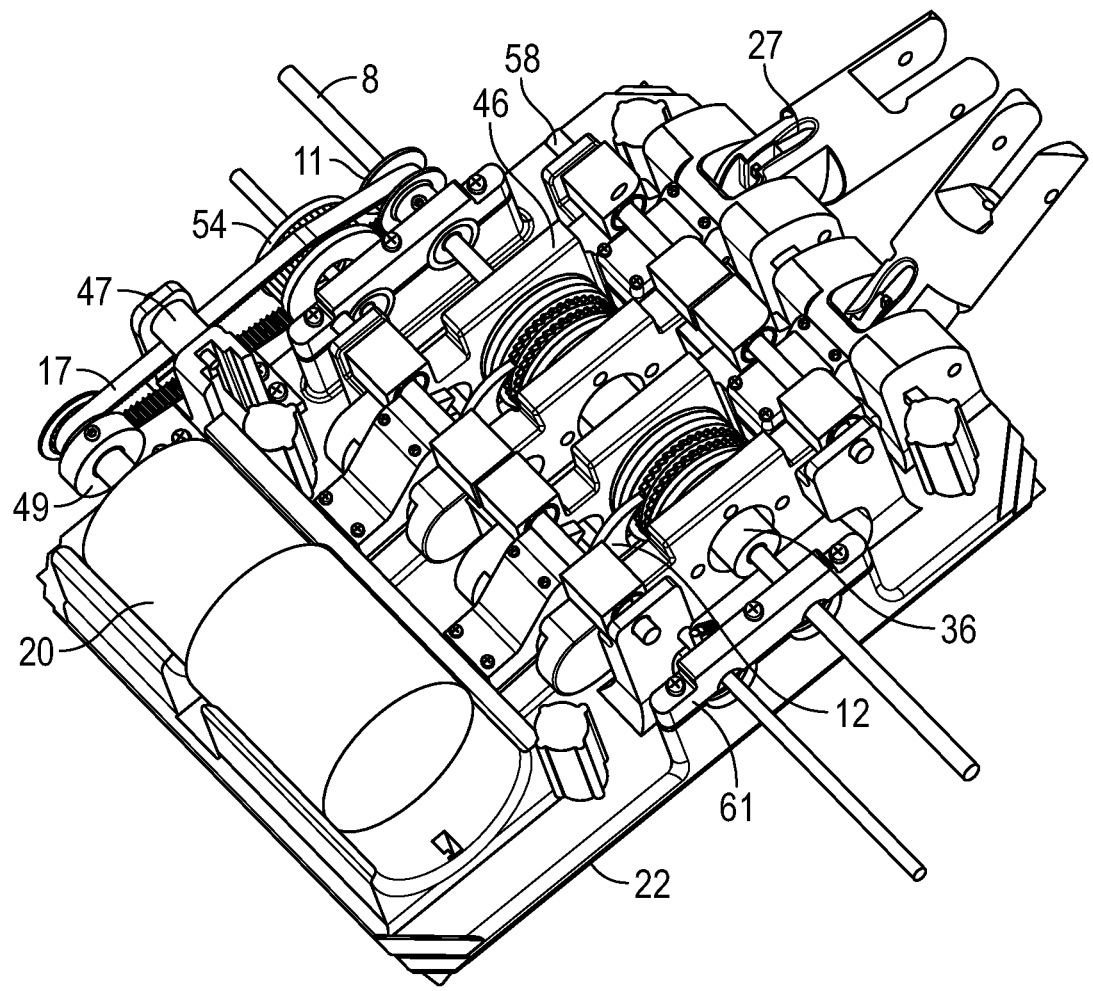
FIG. 1 depicts one embodiment of the prosthetic hand using the electromagnetic actuation mechanism for each individual digit control.
Figure 2:
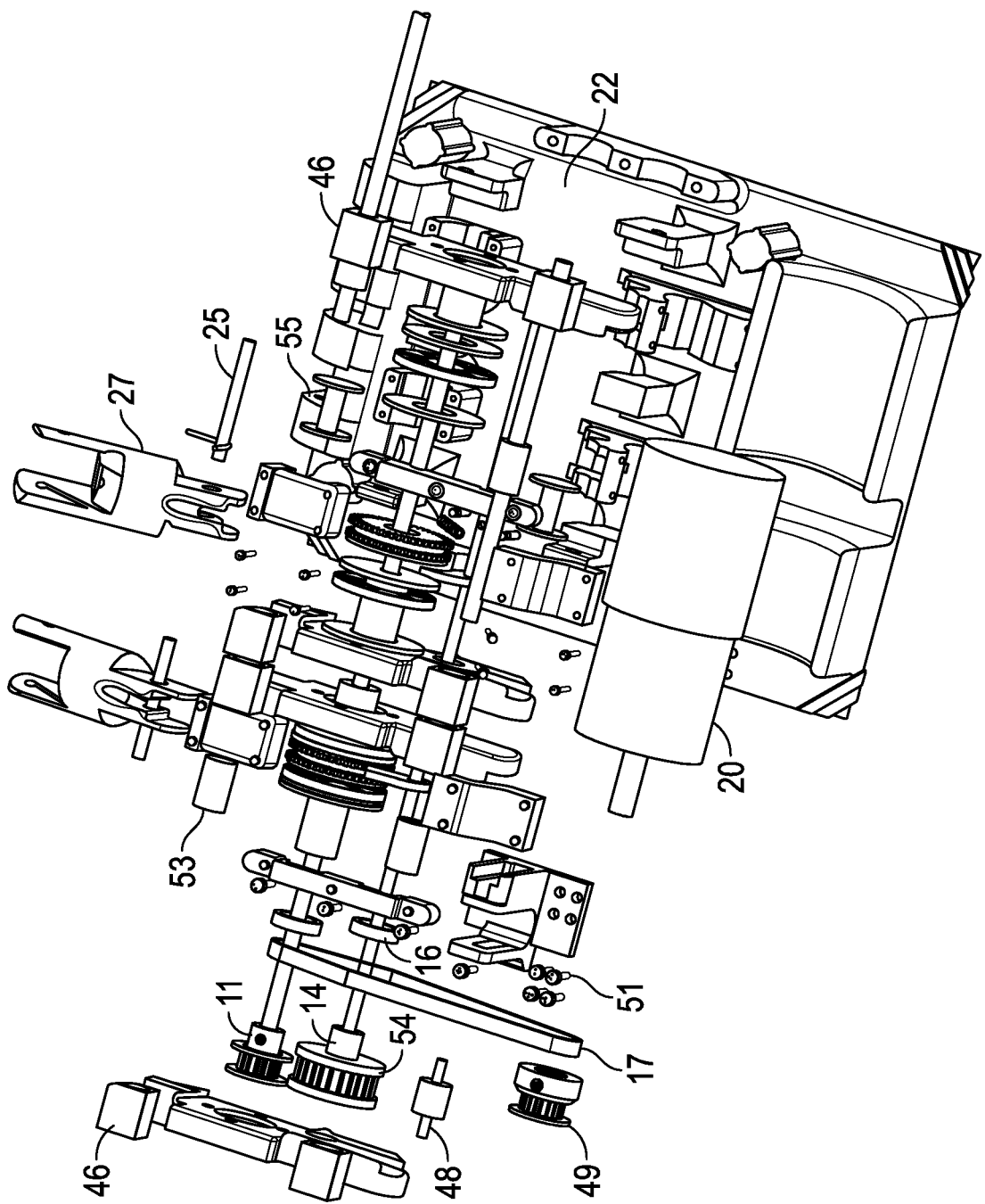
FIG. 2 depicts an exploded view of the parts and components of the prosthetic hand using the electromagnetic actuation mechanism for each individual digit control depicted in FIG. 1. In this exploded view, numerous parts and components of the invention can be seen including, but not limited to, tension shaft 48, motor pulley 49, pawl train pulley 54, one-way bearing 14, radial bearing 16, and cap screws 51, which are used in operating the timing belt 17 as part of the powertrain assembly. This figure also depicts the components for ratchet gear pulley system which drives the operation of the digits.
Figure 3A:
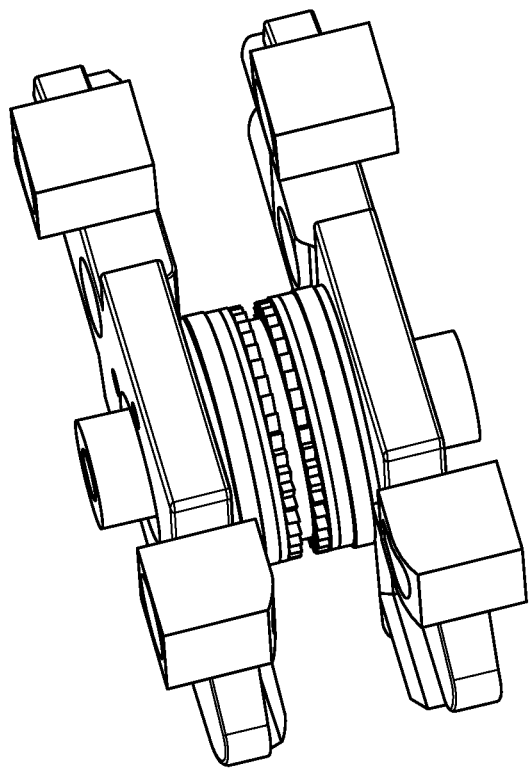
FIG. 3A depicts the clutch pack assembly for the prosthetic hand using the electromagnetic actuation mechanism.
Figure 3B:
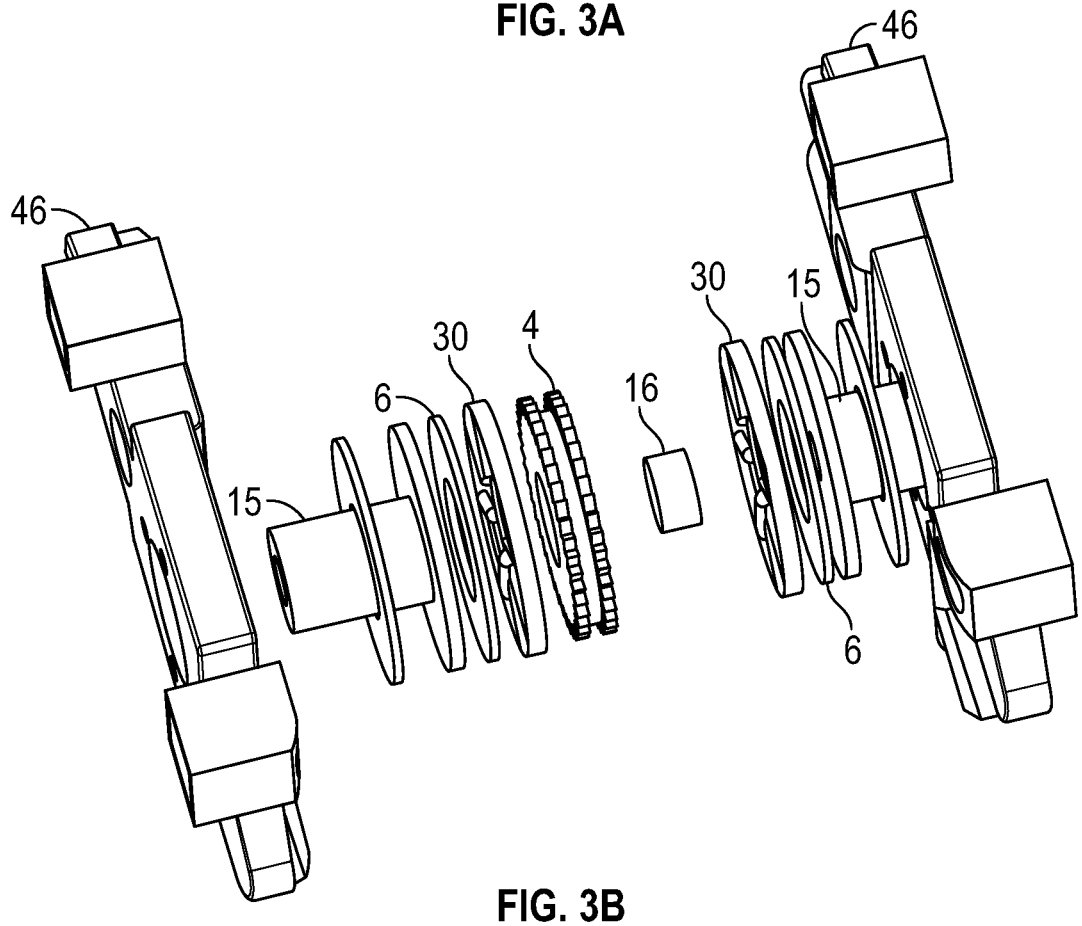
FIG. 3B depicts an exploded view of the clutch pack assembly shown in FIG. 3A. The clutch pack assembly is comprised of pusher plates 46, flanged spline nuts 15, rubber washers 6, ratchet gear 4, radial bearing 16, and thrust bearings 30.
Figure 4A:
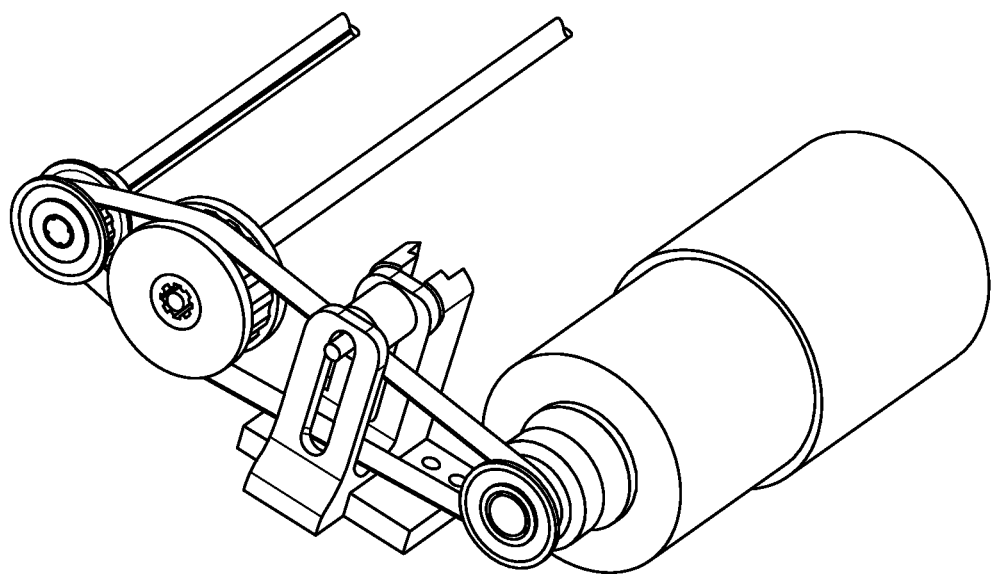
FIG. 4A depicts the powertrain assembly for the prosthetic hand that implements the electromagnetic actuation mechanism.
Figure 4B:
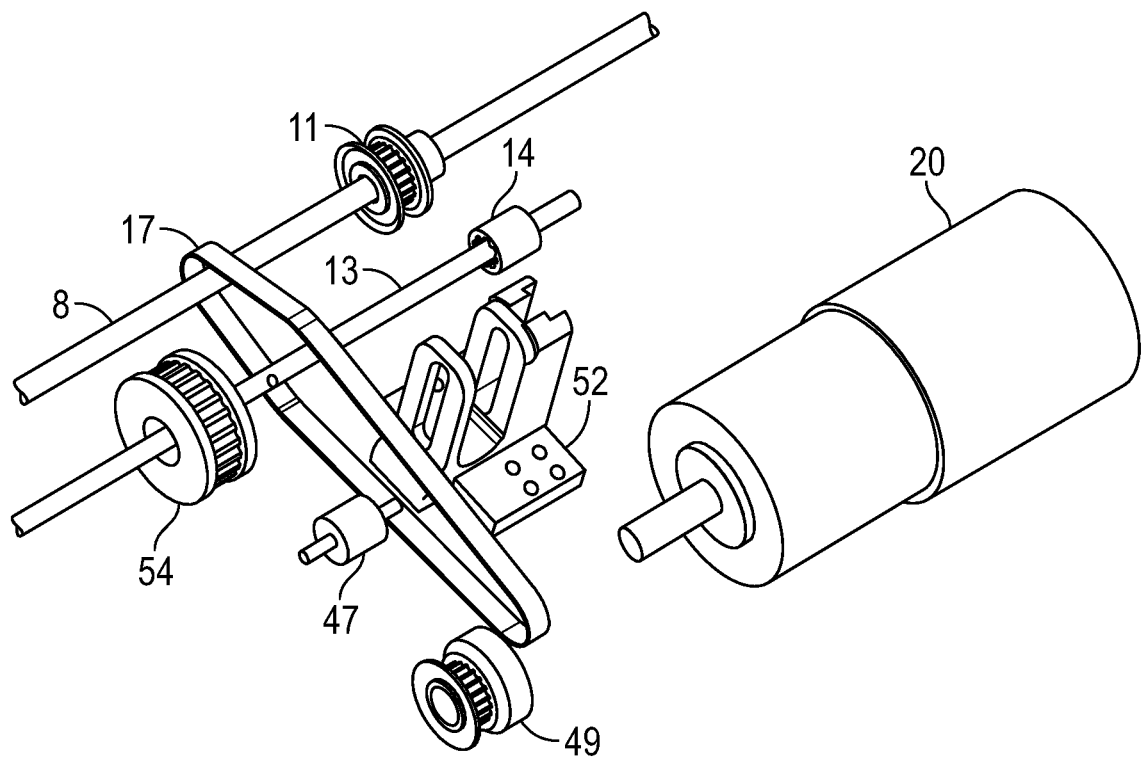
FIG. 4B depicts an exploded view of the powertrain assembly shown in FIG. 4A. The powertrain assembly is comprised of spline shaft 8, timing belt 17, spline shaft pulley 11, pawl train pulley 54, tension bracket 52, one-way bearing 14, tension roller 47, motor pulley 49, and the motor 20.
Figure 5A:
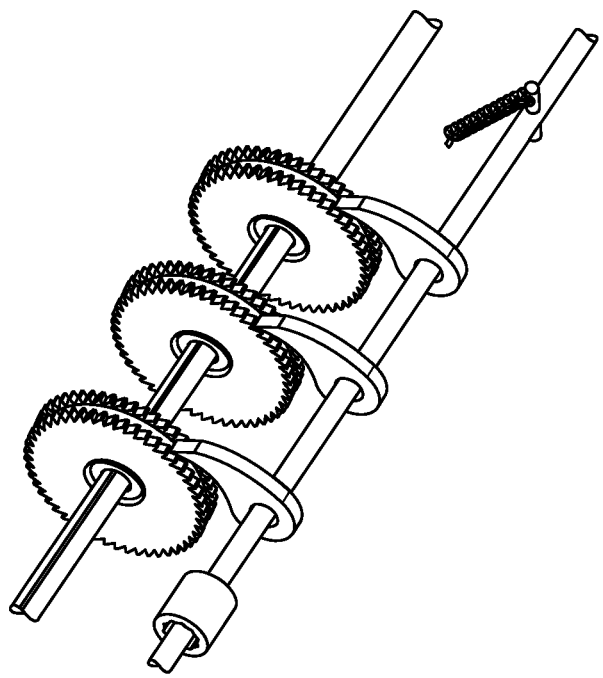
FIG. 5A depicts the ratchet gear and pawl assembly used for locking the individual digits of the prosthetic hand that implements the electromagnetic actuation mechanism.
Figure 5B:
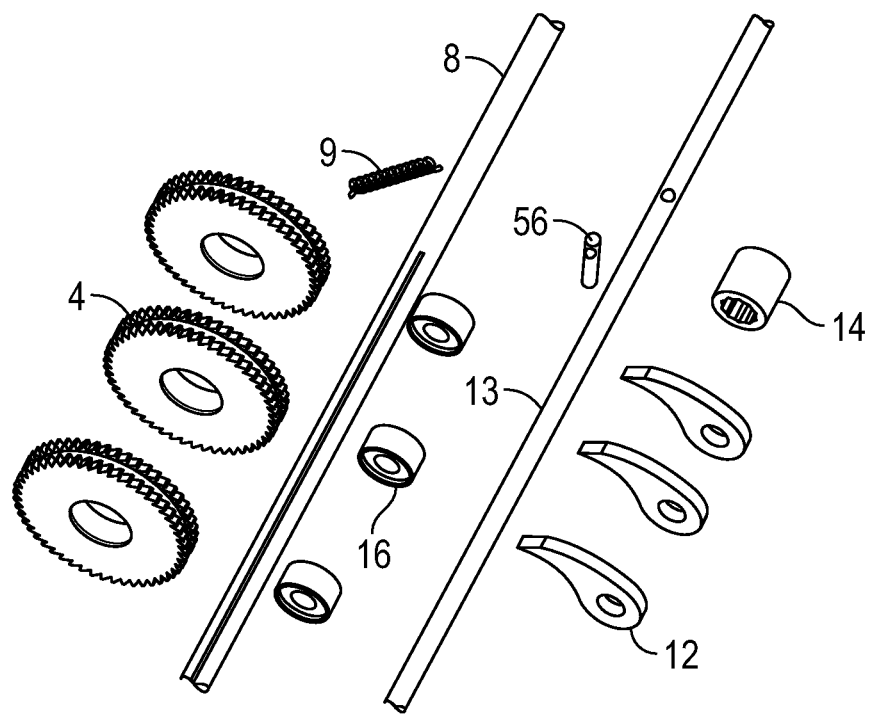
FIG. 5B depicts an exploded view of the ratchet gear and pawl assembly shown in FIG. 5A. The ratchet and pawl gear assembly is comprised of ratchet gears 4, pawl shaft spring 9, spline shaft 8, radial bearings 16, tension anchor 56, pawl train shaft 13, one-way bearing 14, and pawls 12.
Figure 6A:
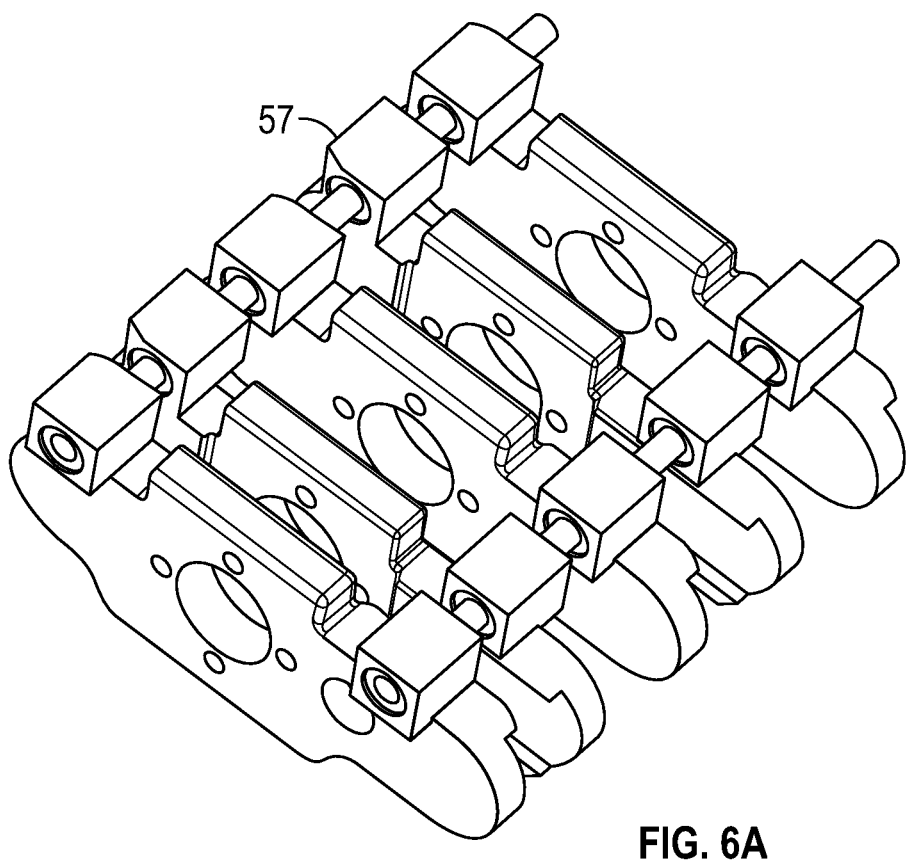
FIG. 6A depicts the linear rail system 57 for the prosthetic hand using the electromagnetic actuation mechanism.
Figure 6B:
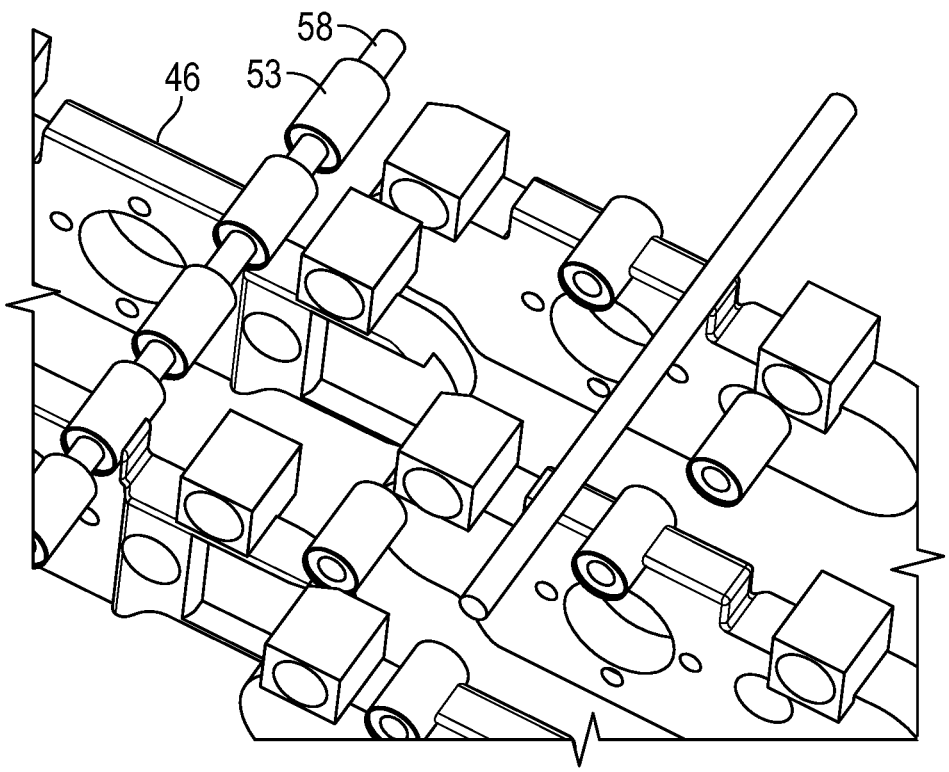
FIG. 6B depicts an exploded view of the linear rail system shown in FIG. 6A. The linear rail system 57 is comprised of pusher plates 46, linear bearings 53, and the guide rail 58.
Figure 7A:
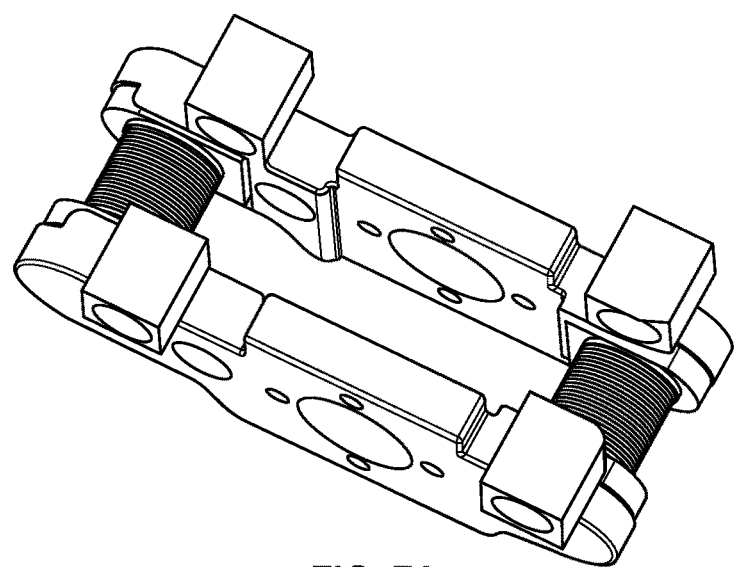
FIG. 7A depicts the electromagnetic coil system for the prosthetic hand using the electromagnetic actuation mechanism.
Figure 7B:
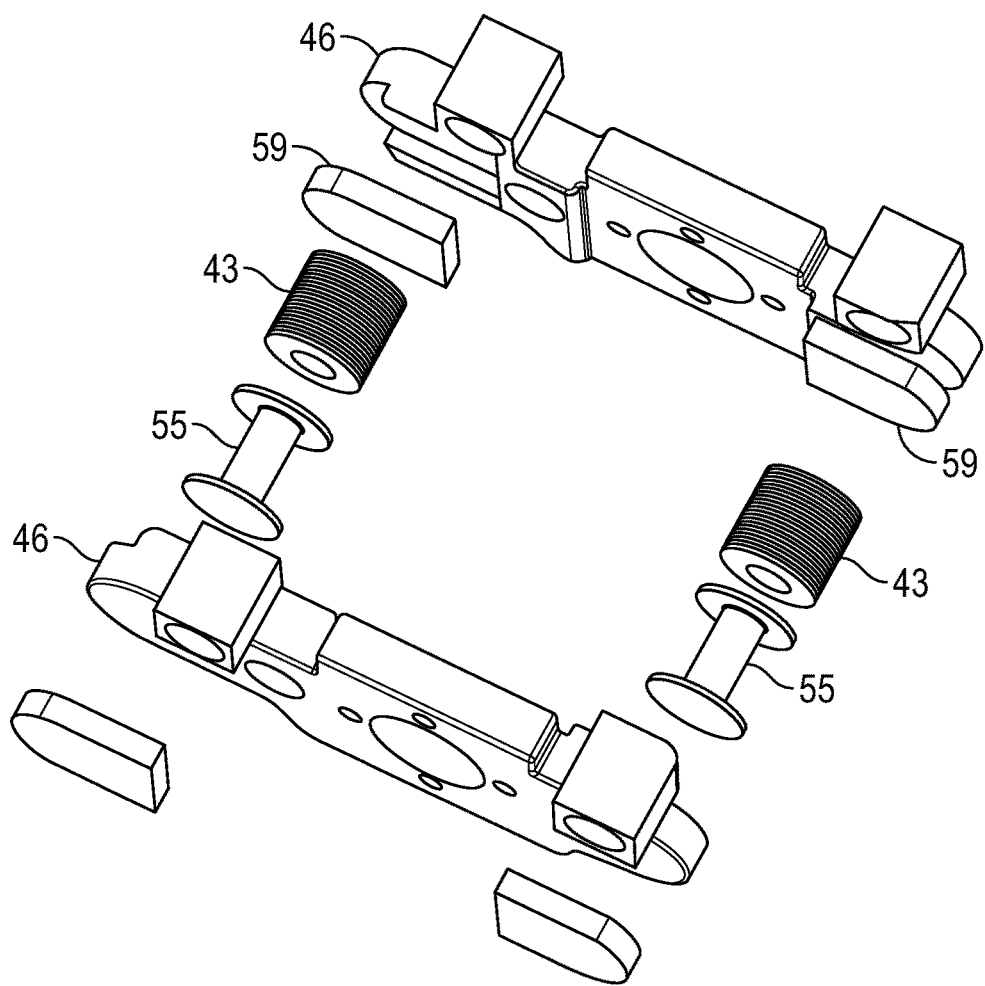
FIG. 7B depicts an exploded view of the electromagnetic coil system shown in FIG. 7A. The electromagnetic coil system is comprised of pusher plates 46, electromagnetic coil cores 55, magnetic steels 59, and electromagnetic coils 43.
Figure 8A:
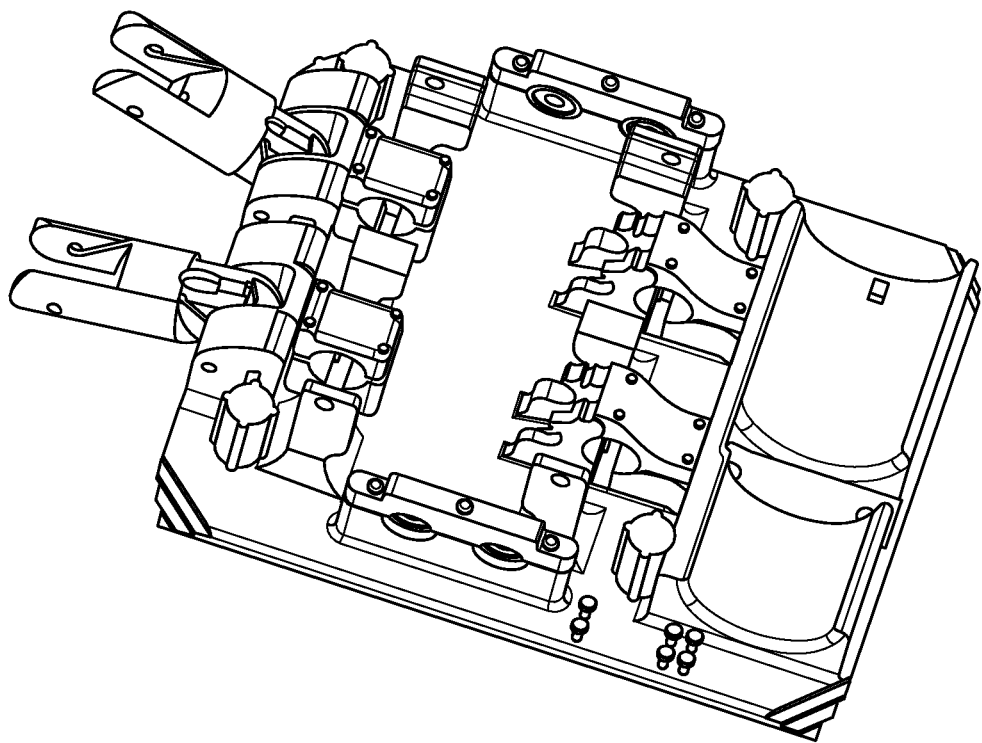
FIG. 8A depicts the structural components for the assembly of the prosthetic hand using the electromagnetic actuation mechanism.
Figure 8B:
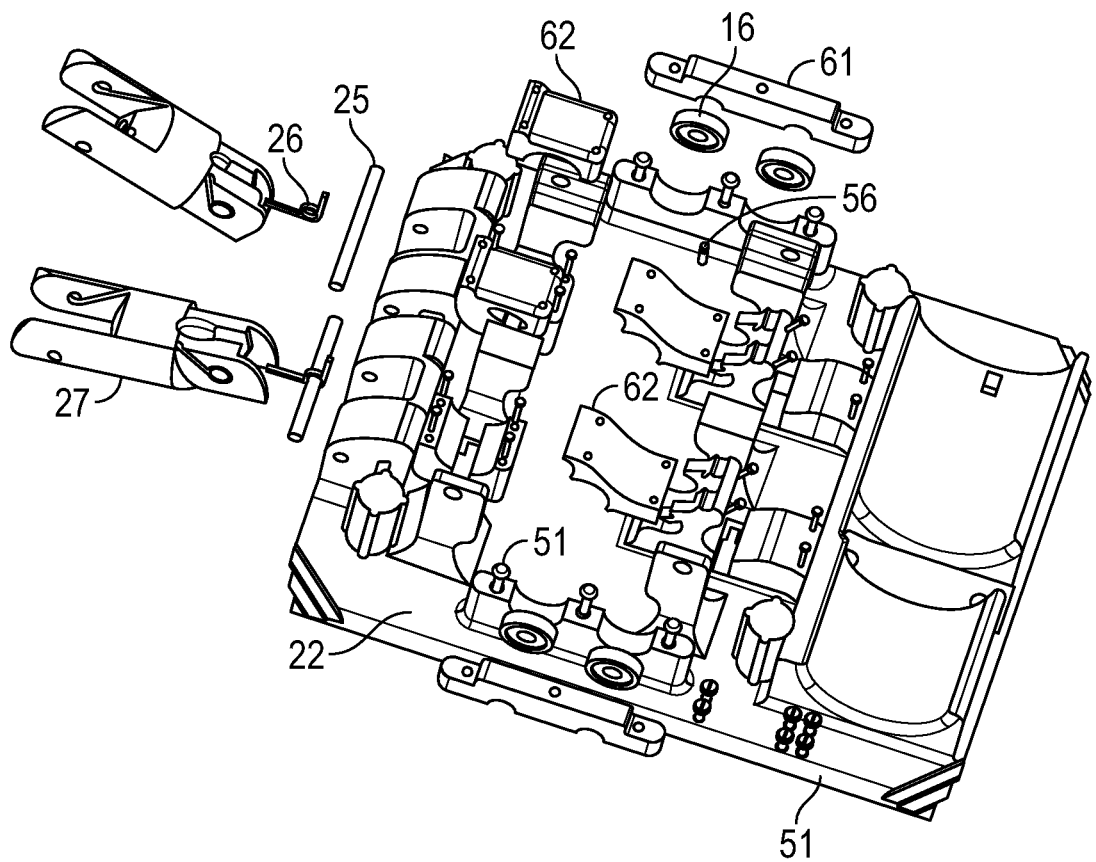
FIG. 8B depicts an exploded view of the structural components of the assembly shown in FIG. 8A. The structural components of the assembly include intermediate phalange 27, torsion spring 26, finger rod 25, coil covers 62, bearing cap 61, radial bearings 16, mechanism platform 22, and cap screws 51.
Figure 9:
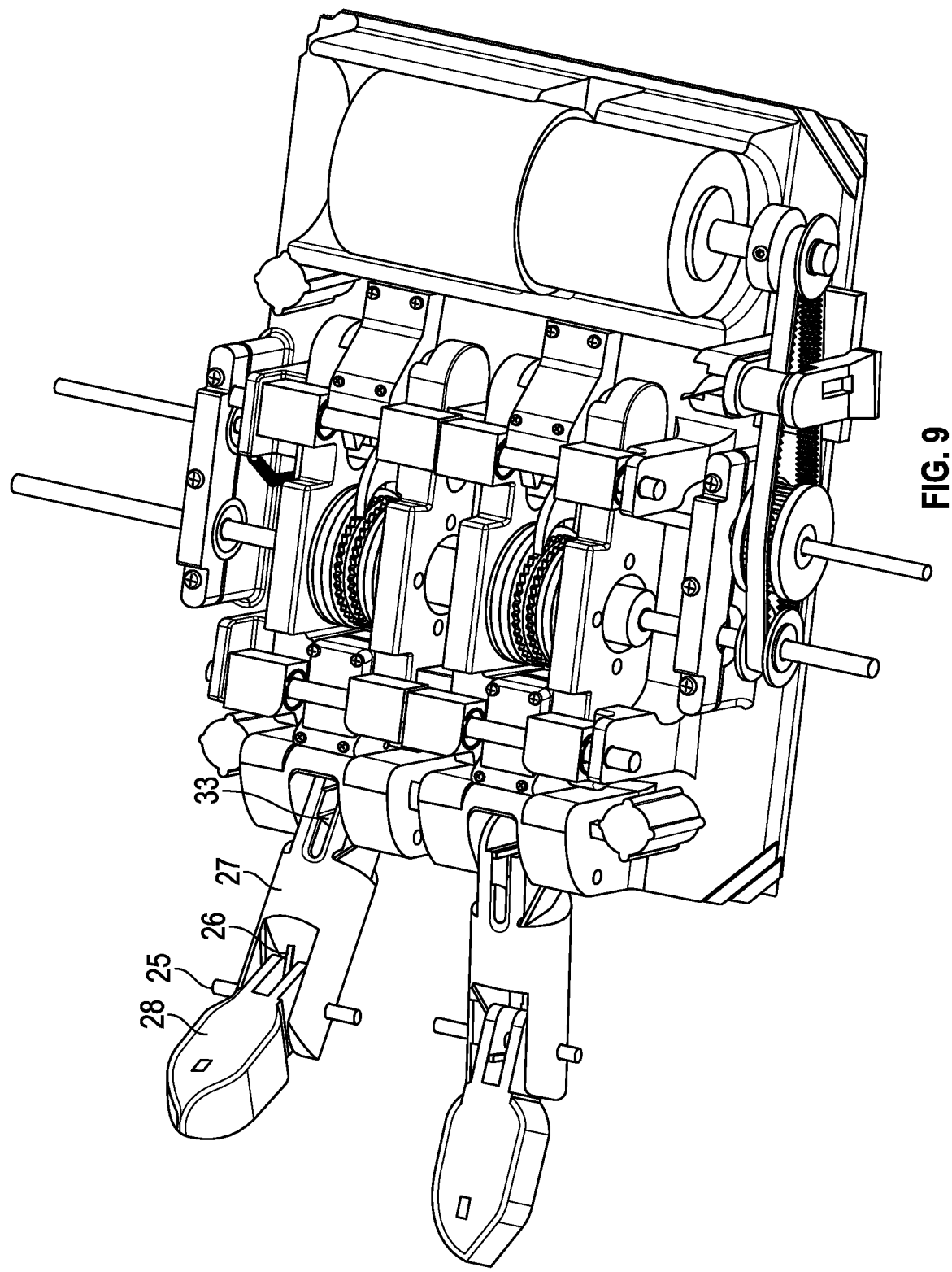
FIG. 9 depicts the embodiment of the prosthetic hand using the electromagnetic actuation mechanism shown in FIG. 1 with the additional finger assembly. The additional finger assembly comprises finger cable 3, torsion spring 26, finger rod 25, intermediate phalange 27, proximal phalange 33, and distal phalange 28. In an additional embodiment, the proximal phalange, and intermediate phalange are all one singular piece instead of different pieces.
Figure 10:
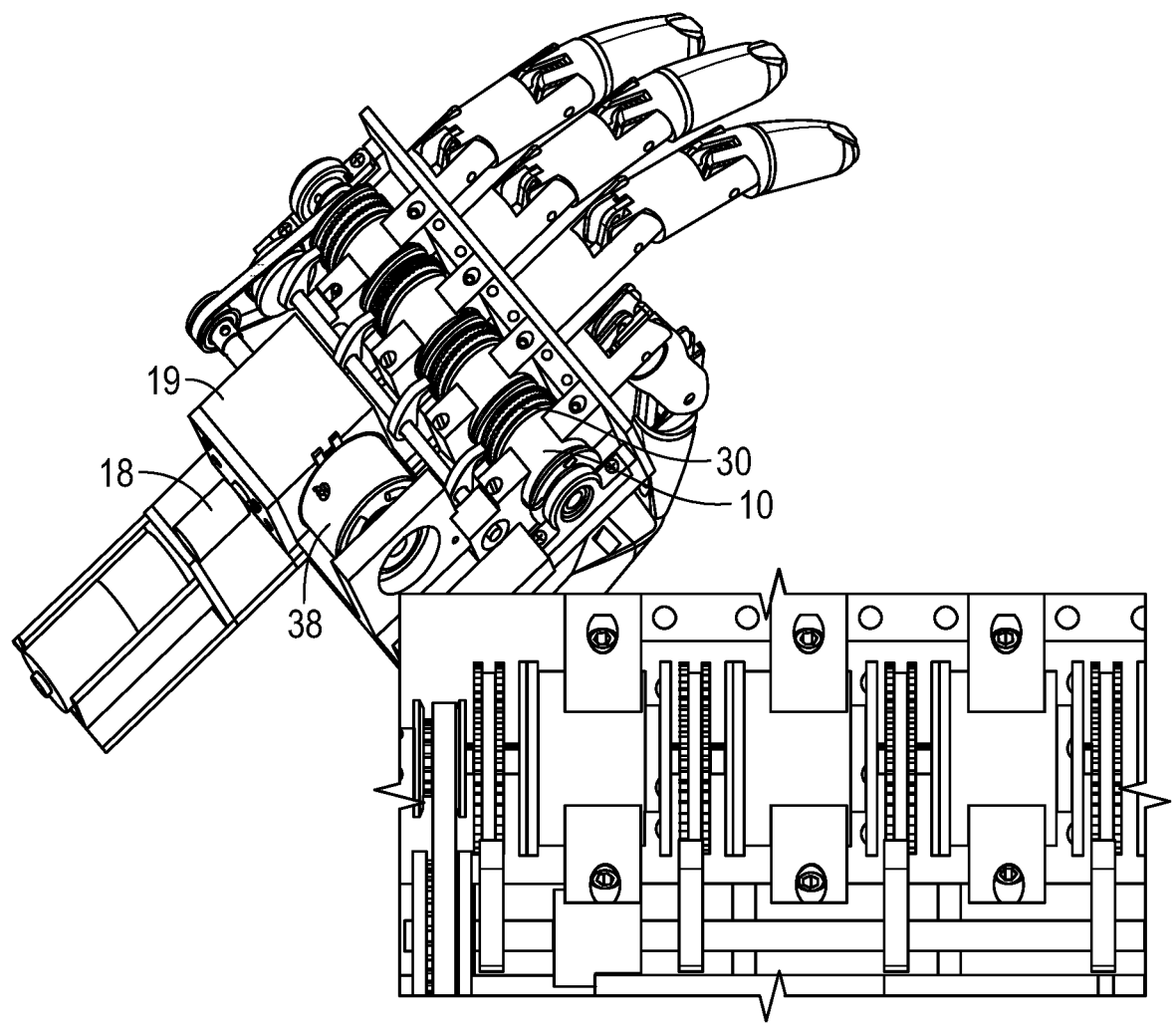
FIG. 10 depicts an additional embodiment of a prosthetic hand using the electromagnetic actuation mechanism for each individual digit control.
Figure 11A:
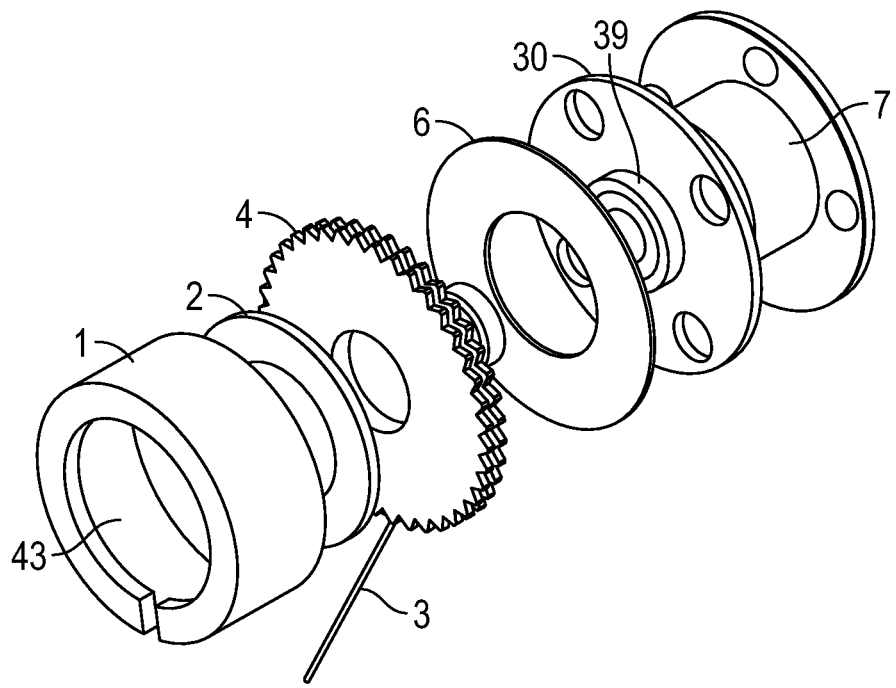
FIG. 11A shows an exploded view of the embodiment depicted in FIG. 10 using the electromagnetic rotary solenoid clutch ("ERSC") with the ratchet gear. The ERSC comprises a rotary solenoid and an electromagnetic clutch. The clutch design allows for a splined nut attached to the spline shaft to rotate inside of the clutch's hollow magnetic steel core while providing axial motion through use of electromagnetic forces. The ERSC assembly 10 with the ratchet gear is comprised of coil casing 1, plastic coil washer 2, finger cable 3, ratchet gear pulley 4, radial bearing 16, rubber washer 6, plunger assembly 7, spline nut 39, thrust bearing 30 and electromagnetic coil 43. Force is transmitted to ratchet gear from the clutch assembly using friction drive principles between the two mating friction surfaces after the electromagnets are engaged (using the ratchet gear and rubber washer).
Figure 11B:
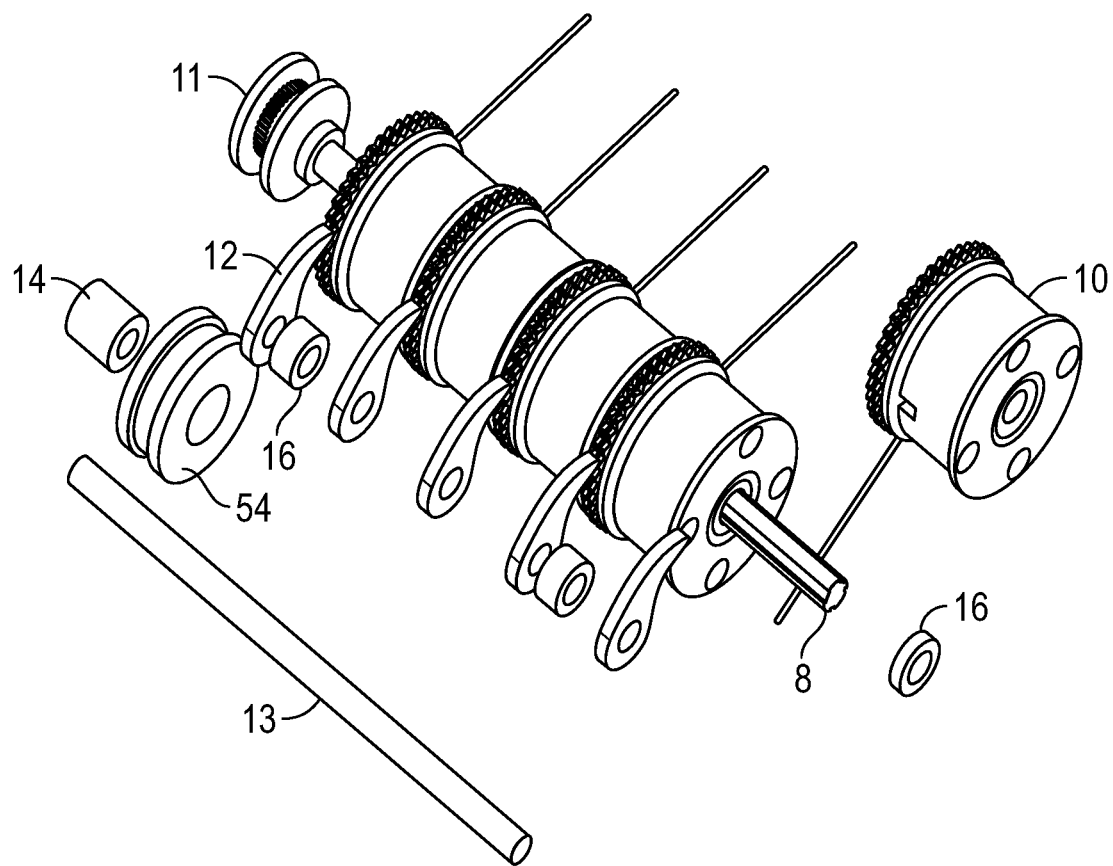
FIG. 11B depicts an exploded view of the ratchet and pawl train and coil assemblies. The ratchet and pawl train and coil assemblies are comprised of radial bearings 16, spline shaft 8, the ERSC assembly 10, spline shaft pulley 11, pawl 12, pawl train shaft 13, one way bearing 14, and pawl train pulley 54.
Figure 12:
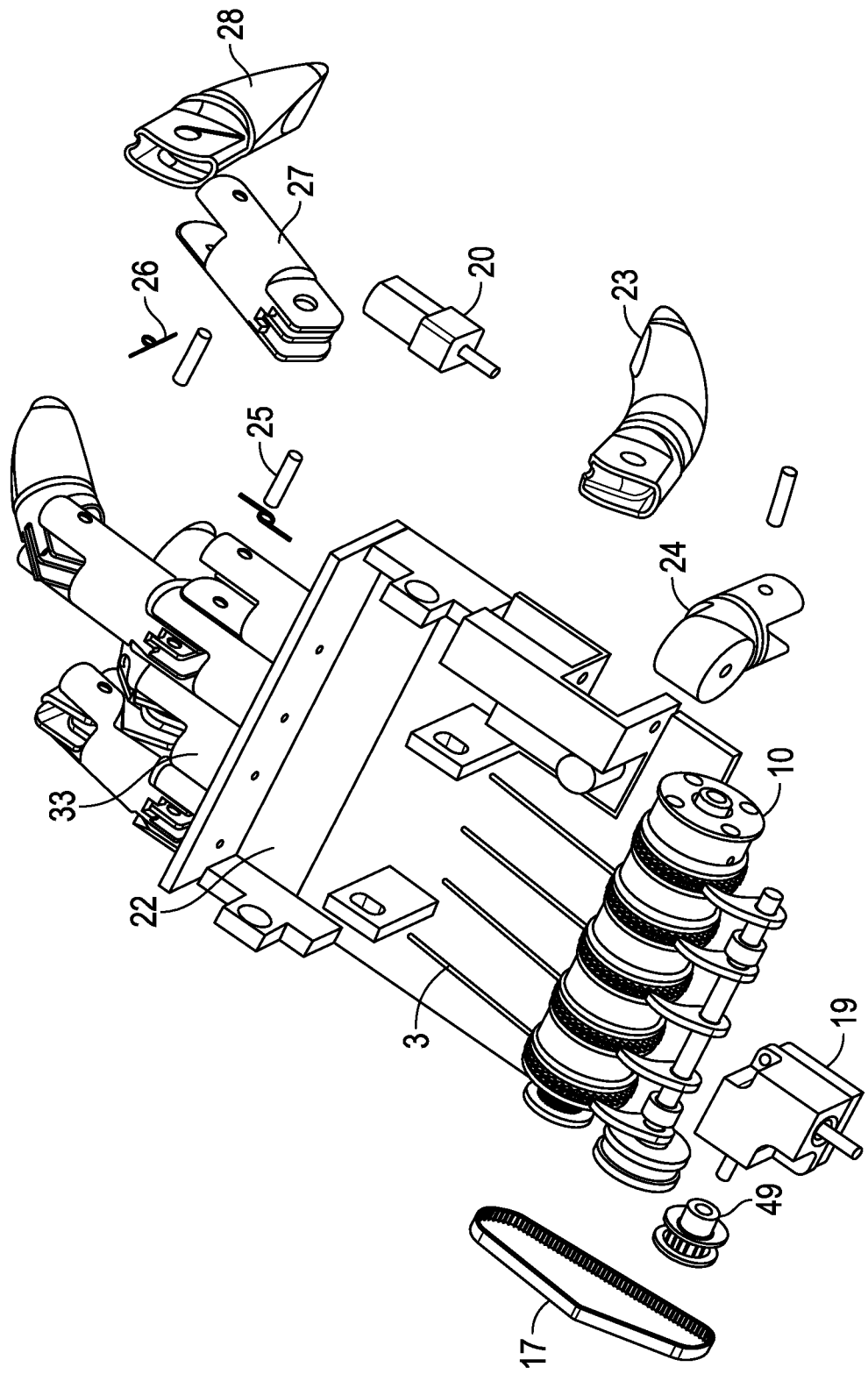
FIG. 12 depicts an exploded view of one embodiment of the configuration of components to construct an additional embodiment of the disclosed prosthetic hand device. This configuration is comprised of pawl train pulley 54, finger cable 3, timing belt 17, motor pulley 49, gear box 19, ERSC assembly 10, a customized mechanism platform 22, thumb tip 23, thumb base 24, finger rod 25, torsion spring 26, intermediate phalange 27, distal phalange 28, proximal phalange 33, and motor 20. In this embodiment, five ERSC assemblies are used, wherein the fifth ERSC assembly provides flexion to the thumb.
Figure 13:
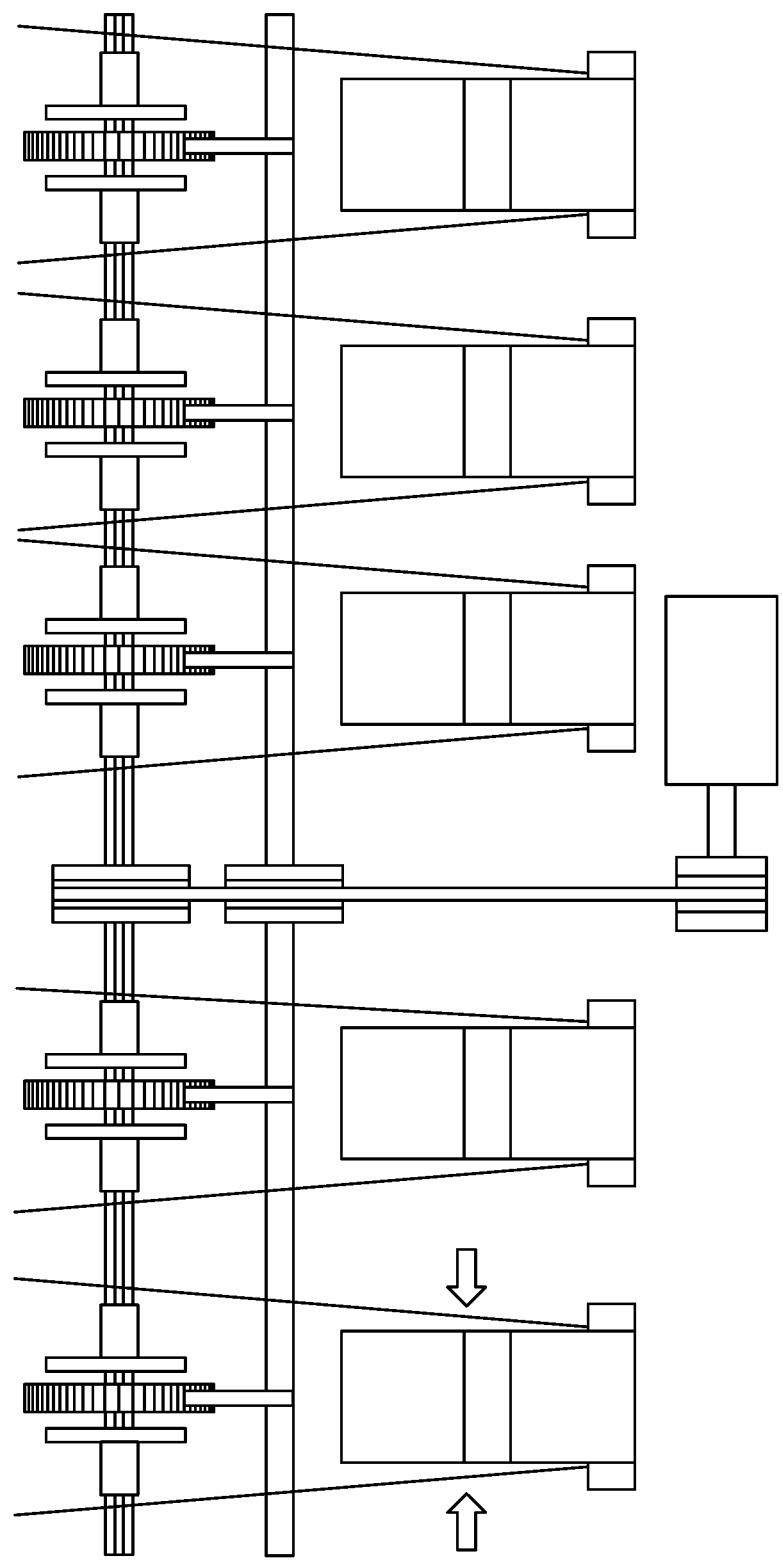
FIG. 13 depicts an additional embodiment of the ELECTROMAGNETIC ACTUATION MECHANISM FOR INDIVIDUAL DIGIT CONTROL OF AN ARTIFICIAL HAND using the spline shaft and spline nut assembly with friction surface and thrust bearing in place of the ERSC assembly. This novel embodiment uses the ratchet and gear pulley system with the spline shaft and spline nut assembly and electromagnets to provide individual digit flexion.
Figure 14:
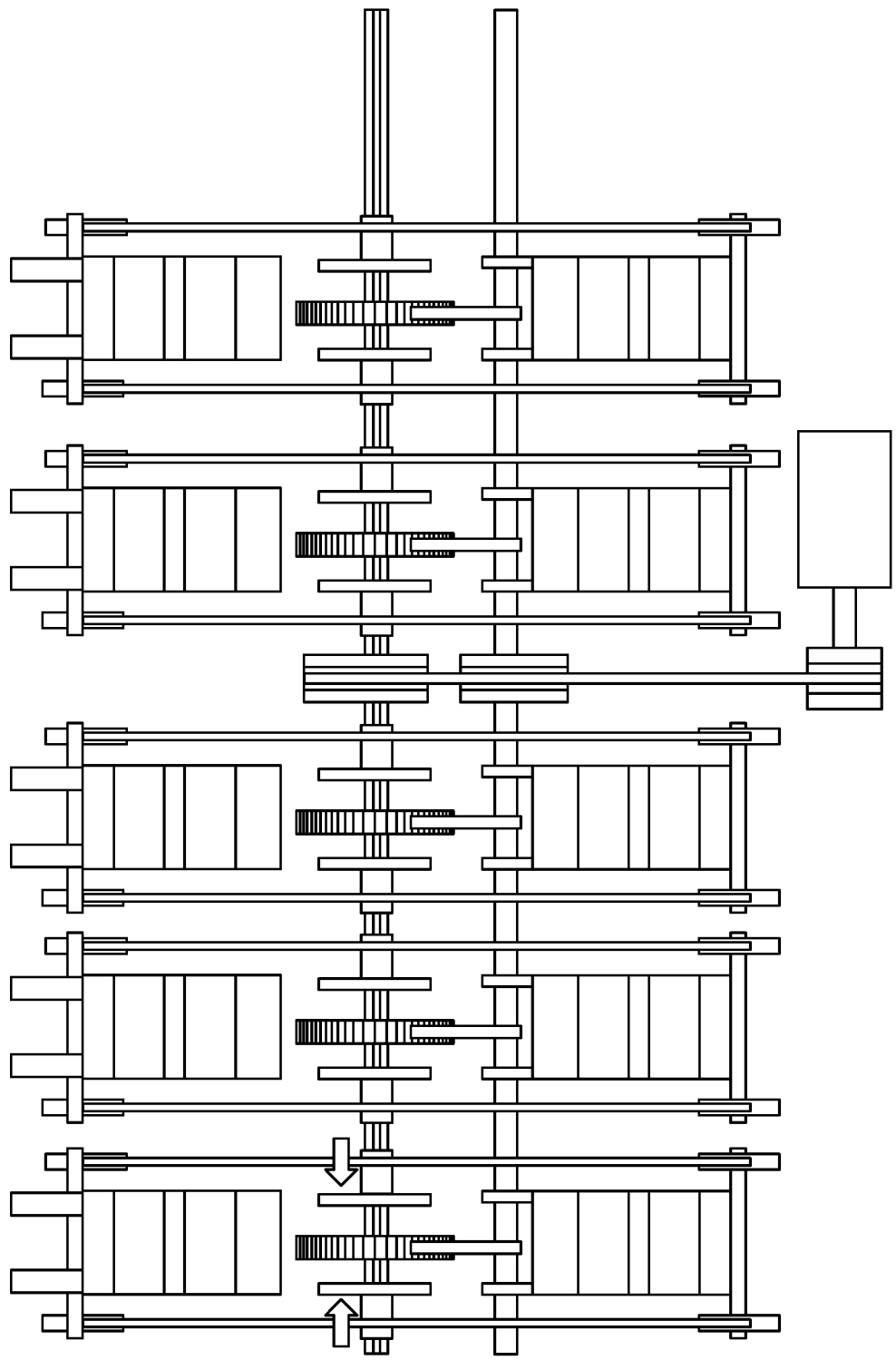
FIG. 14 provides a rendering of an additional embodiment of the ELECTROMAGNETIC ACTUATION MECHANISM FOR INDIVIDUAL DIGIT CONTROL OF AN ARTIFICIAL HAND. This novel embodiment uses the ratchet and gear pulley system with the spline shaft and spline nut assembly and electromagnets to provide individual digit flexion. This embodiment further uses additional electromagnetics in order to provide "digitized" functionality of the fingers. In this embodiment, dual electromagnets are used on each side of the ratchet and gear pulley system.
Figure 15A:
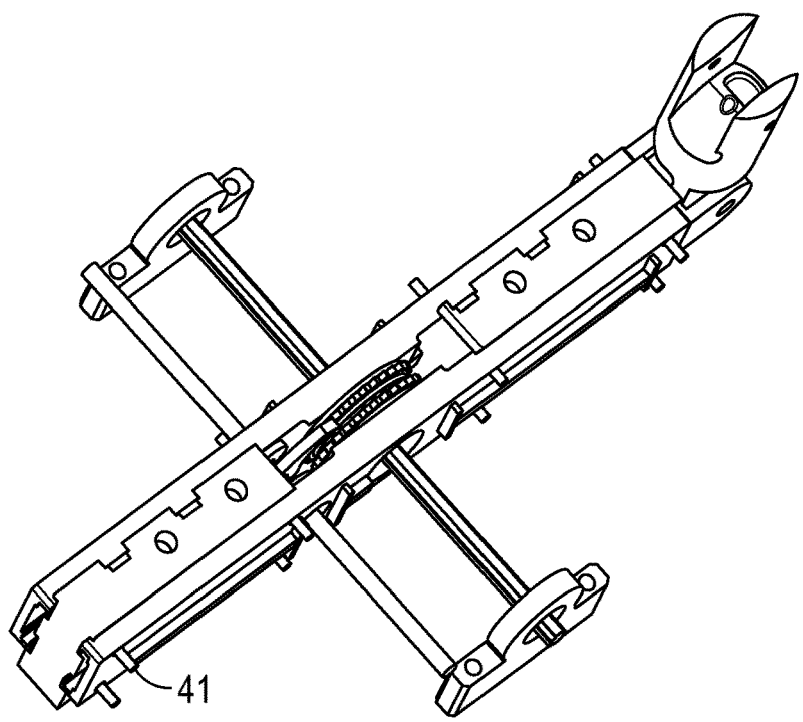
FIG. 15A provides an alternate drawing of the digit unit 41 of the additional embodiment of the invention depicted in FIG. 14 that shows the various components of the digit unit.
Figure 15B:
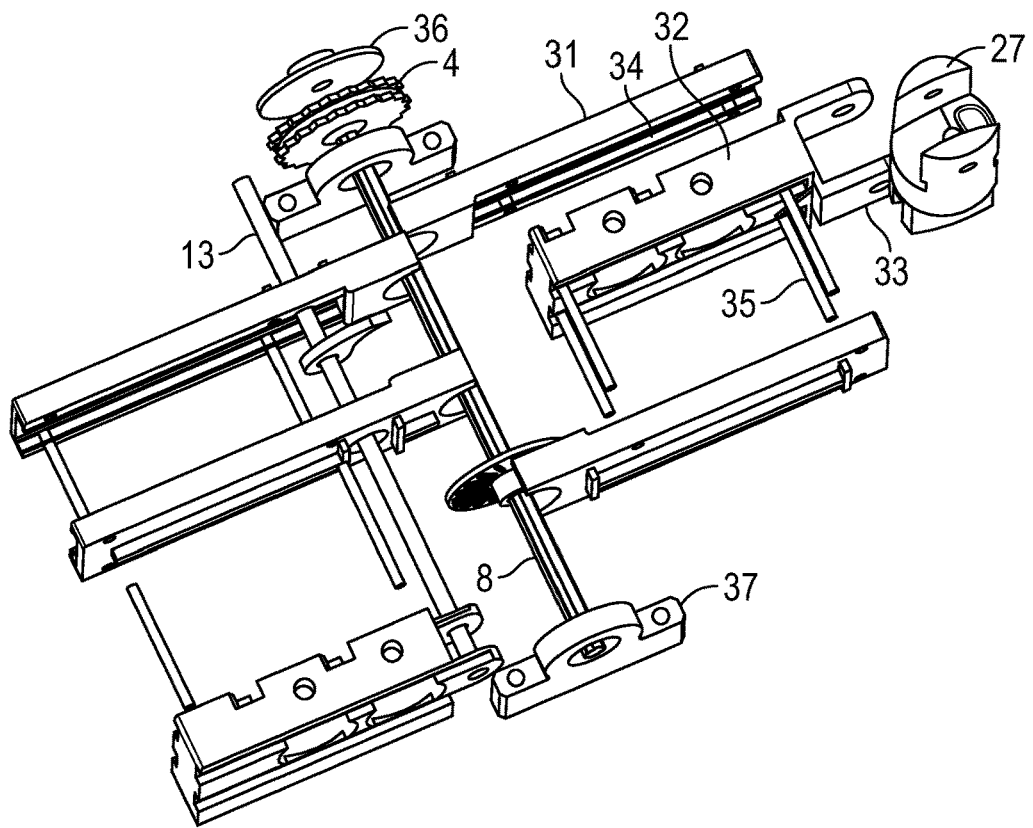
FIG. 15B provides an exploded view of the alternate drawing of the digit unit of the additional embodiment of the invention depicted in FIG. 14. As shown, the digit unit is comprised of pawl train shaft 13, spline nut assembly 36, ratchet gear 4, clutch fork 31, magnetic pole 34, coil housing 32, rail tubing 35, proximal phalange 33, intermediate phalange 27, spline shaft 8, and bearing block 37.
Figure 16A:
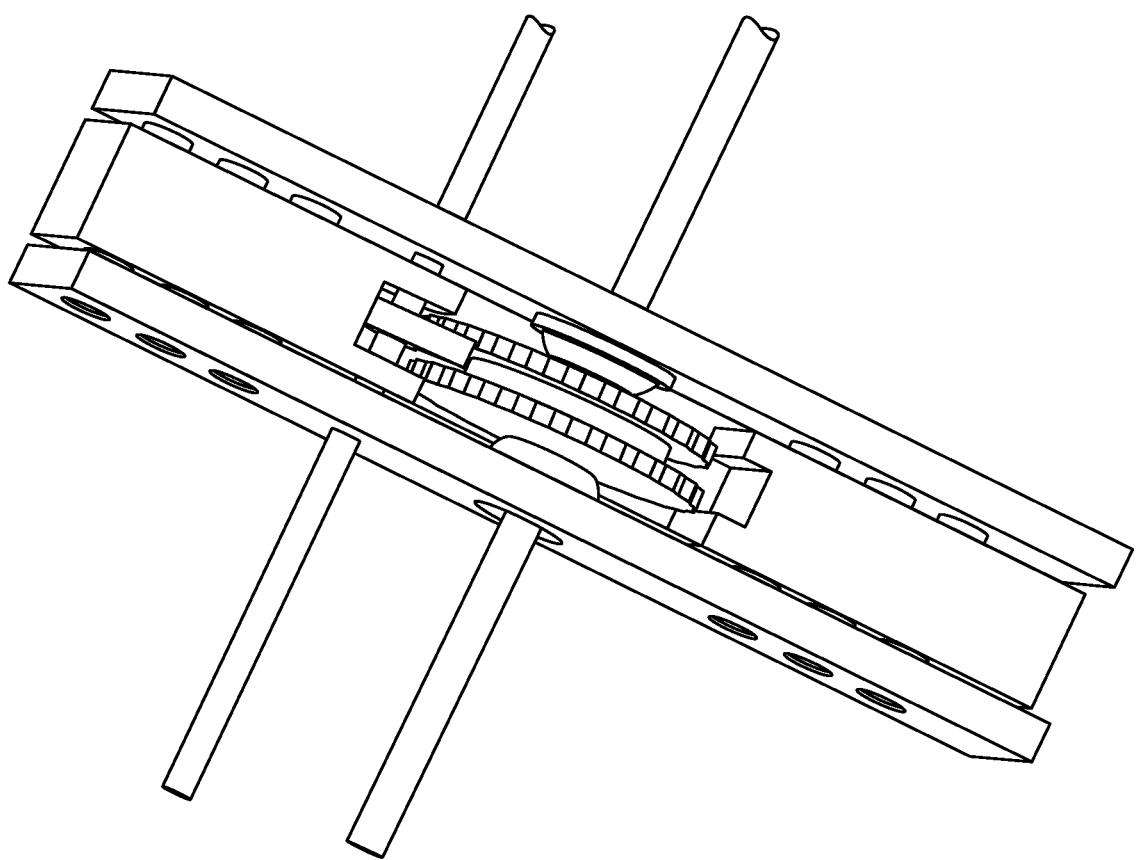
FIG. 16A provides an alternative view of the digit unit of the additional embodiment of the invention depicted in FIG. 14.
Figure 16B:
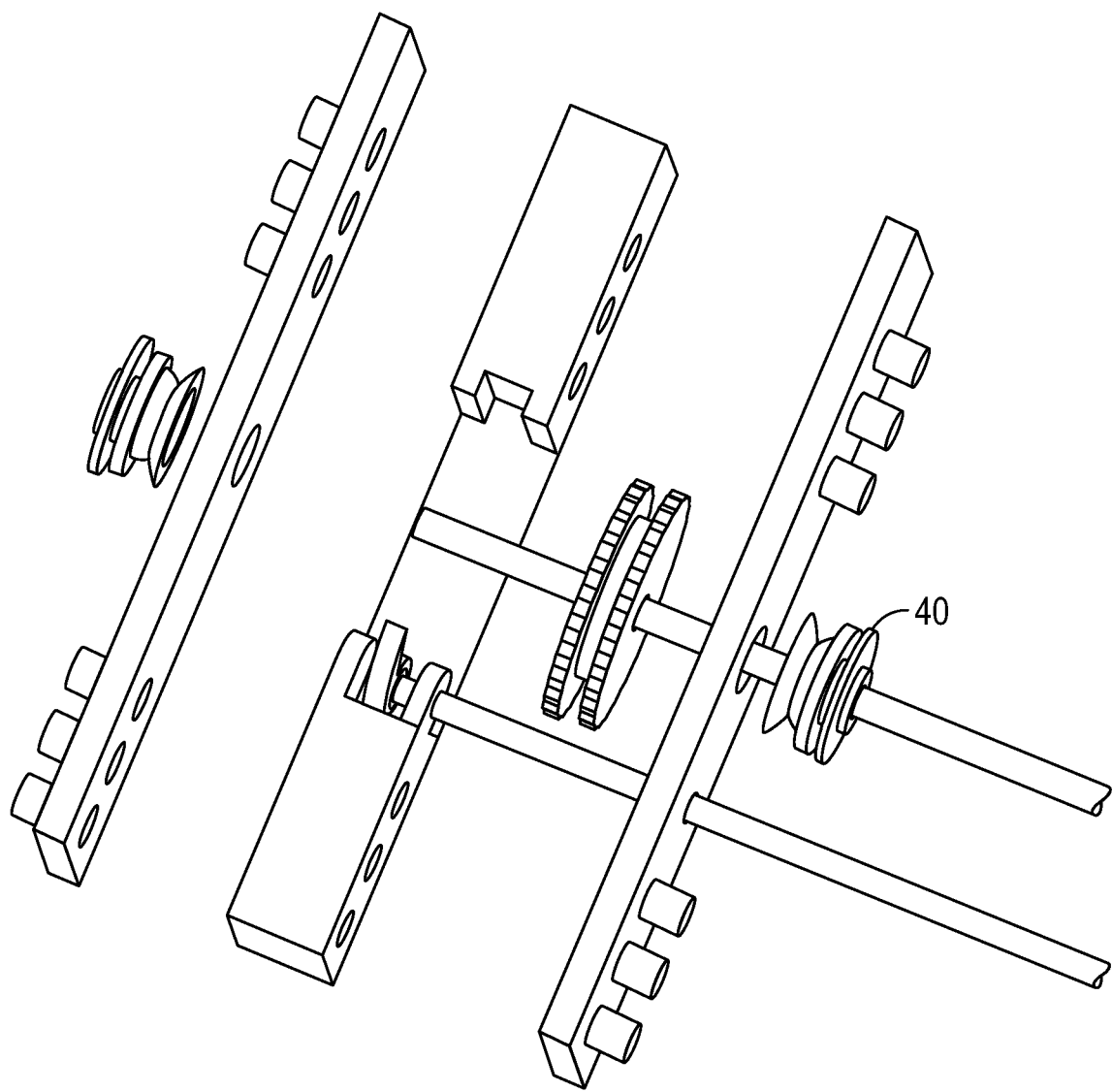
FIG. 16B provides an alternative view of the digit unit of the additional embodiment of the invention depicted in FIG. 14.
Figure 17A:
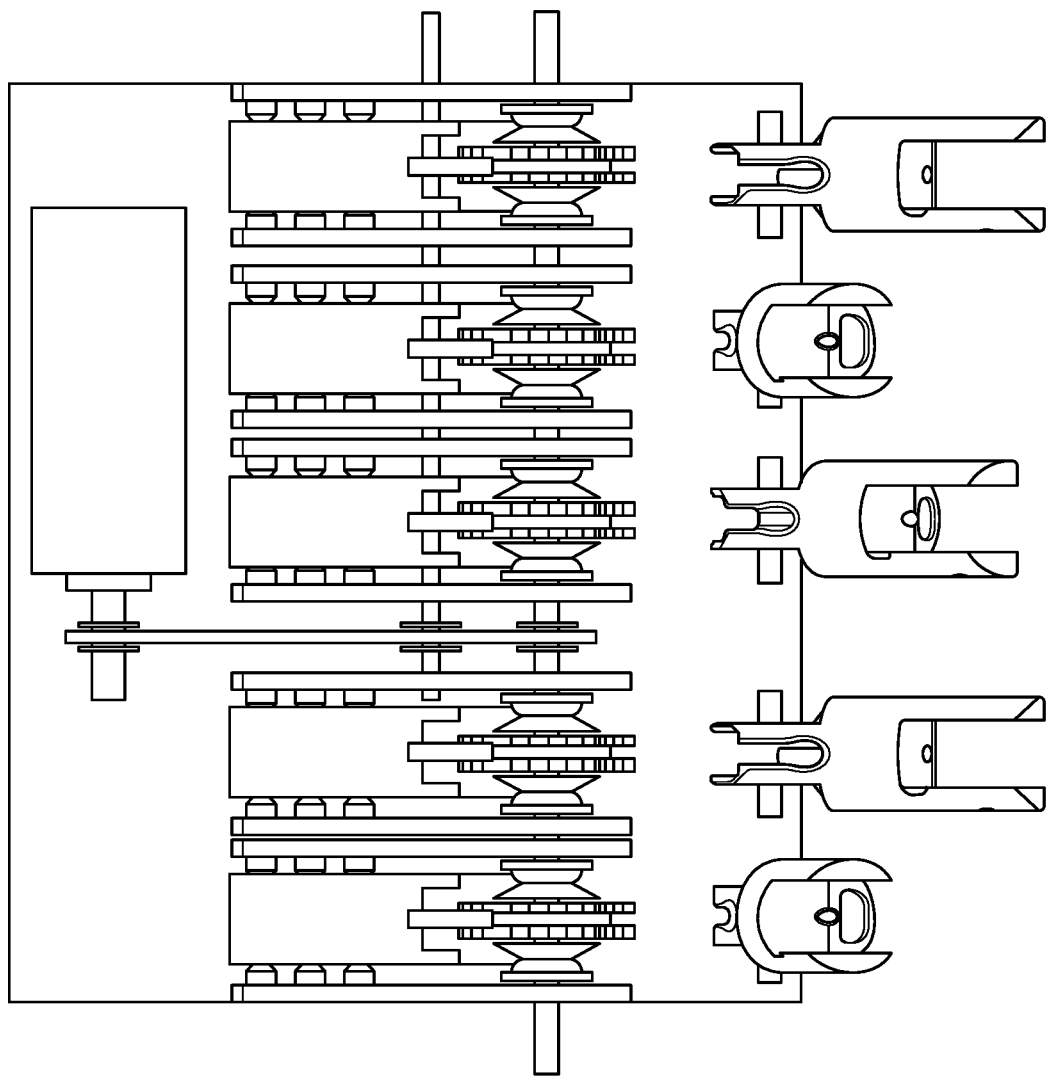
FIG. 17A provides an embodiment of the iteration of mechanisms for individual digits and their design assembly for digit flexion of the ELECTROMAGNETIC ACTUATION MECHANISM FOR INDIVIDUAL DIGIT CONTROL OF AN ARTIFICIAL HAND.
Figure 17B:
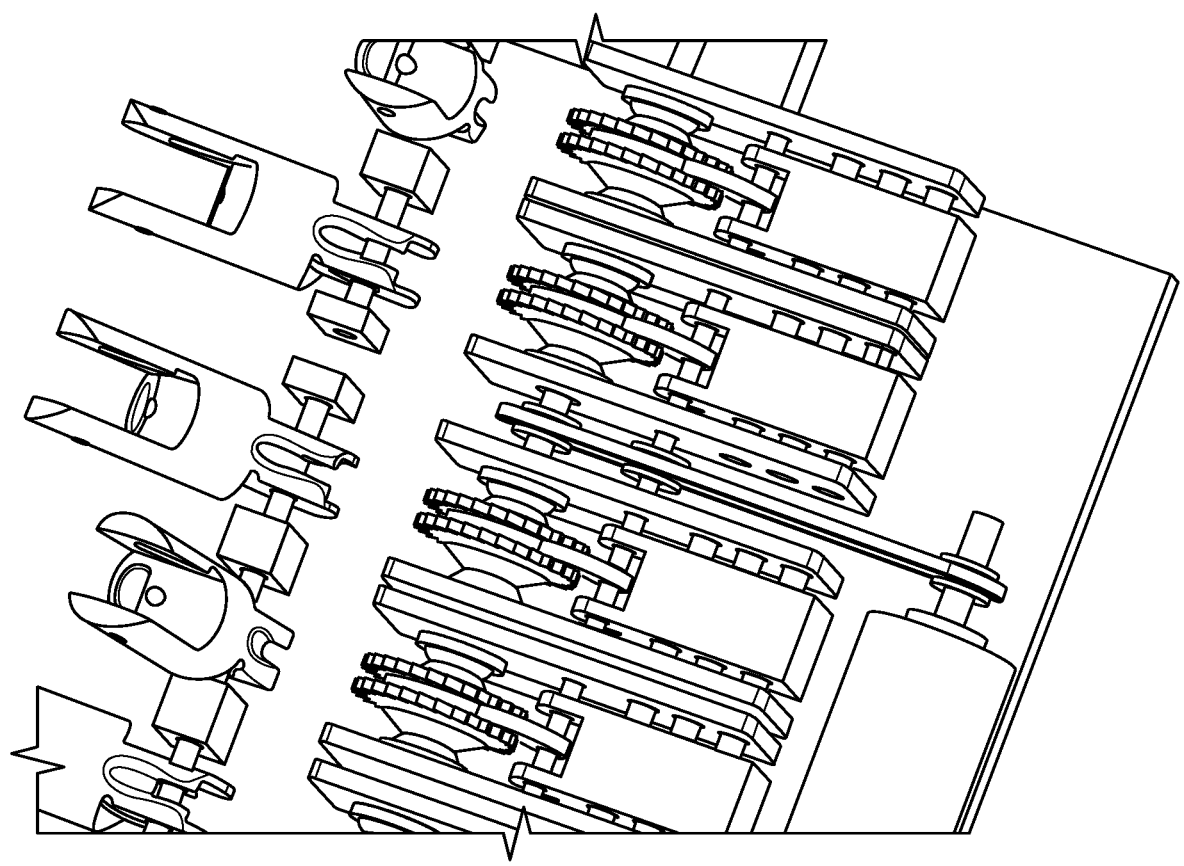
FIG. 17B provides an alternative view of an embodiment of the iteration of mechanisms for individual figures and their design assembly for digit flexion show in FIG. 17A.

The disclosed invention is an innovative, cost-efficient driving mechanism for the prosthetic hand industry which makes use of only one motor to individually control flexion movements of each digit including the thumb of a prosthetic hand separately. While the preferred embodiment employs a DC motor, those skilled in the art will recognize that the disclosed invention may also be driven by an AC motor or other applicable drive motor. This design has several advantages over current commercially available prosthetic hand devices and has the potential to contribute greatly to the field of prosthetics and significantly impact the life of a suffering amputee. This mechanism decreases the weight of the prosthetic, reduces the size, minimizes noise, reduces the power usage, increase functionality, increases the speeds and forces, and orients the parts of the devices in a manner that creates an aesthetically appealing design.

This application discloses an innovative prosthetic hand apparatus that is comprised of an artificial hand configuration comprising at least two individual digits, a single motor 20, a magnetic actuation system, locking mechanism, and a spline nut 39 and shaft 8 configuration. For the hand apparatus, all individual digits are each spring loaded and each has its own separate ratchet and pawl pair mechanism. The ratchet gears 4 are on the main shaft as with the spline shaft 8 and spline nut assembly 36, and the pawls 12 are located on the secondary shaft, parallel to the main shaft, driven by the timing belt 17 in a directional manner due to the implementation of a one-way bearing 14 on the pawl shaft 13. This one-way bearing 14 allows the pawl train shaft 13 to remain stationary in one direction and transmit torque in the other. During operation of the apparatus, the drive spline shaft 8 spins with the ratchet gears 4 engaged by the spline nuts 39 via the pusher plates 46 of the magnetic actuating system, causing the pawl 12 to ratchet on top of the ratchet gear 4 until the shaft stops spinning. Once static, the pawl 12 is engaged into one of the teeth of the ratchet gear 4, causing it to "lock" in place for a grasp to be "held." This attribute is innovative due to the fact that certain prosthetic hands have a motor brake or shaft brake that locks all digits together (not individually), causing a loss in functionality and dexterity. Additionally, most prosthetic hands do not have a locking mechanism like the one disclosed and instead rely on the rigidness of a motor gearbox to lock the digits into place.

Having the ability to lock each individual digit also allows for each digit to be released individually in any combination. The pawl train mechanism operates via a one-way bearing 14 and pawl train pulley 54 assembly. From the drive-end side, the pawl shaft one-way bearing 14 free spins in the counter clock-wise direction as the digits are manipulated, but applies torque to the pawl shaft 13 in the clockwise direct. So, when all digits are locked into place to achieve a specific grasp or hand function, turning the motor 20 one iteration backwards releases the pawls 12 from all of the ratchet gears 4 and allows the digits to "spring back" to the open-palm position via torsion springs 26 placed in the joints of the fingers. This allows for the fingers to spring back to the natural open position without noise and without any power provided by the motor, which increases battery life. Moreover, the unique specific pawl angle and geometry, with respect to the teeth of the ratchet gear, allow for solid yet quiet engagement with quick and effortless disengagement.

The ratchet and pawl locking mechanism is "non-backdrivable." "Non-backdrivable" is a term known in the art meaning to have no motion in the opposite direction of the grasp due to external loads. When an opposing load is applied to the digit, the mechanism or motor does not "give-in", spin, or shift backwards. This function of the hand is desirable when dealing with static grips, slip detection, and holding various objects. Other known devices that have individual motors for each digit rely on the rigidness of the motor shaft to prevent motion in the opposite direction. When the loads overload the motor, the shaft is forced to spin backwards. This can potentially cause damage to the unit and allows for slippage of the object to occur.

The self-releasing digits do not require motor engagement to return to the open position due to the use of torsion spring 26 in the intermediate phalange 27, distal phalange 28, and proximal phalange 33 of the fingers. In a preferred embodiment the springs will be a dampening spring. A dampening spring is preferred because, when using a regular spring, digits would spring up sporadically in a more unnatural manner, drawing attention to the prosthetic and its user. Many electric prosthetic hands are rejected by users due to the unnatural appearance and movement of the hand and noise of the device. These issues bring negative attention to the user. The combination of the dampening springs and the soft-touch positive locking pawl mechanism provide a more natural movement with less noise.

As disclosed above, the digits can be sprung back into the open position without the use of the motor. However, in an additional embodiment, the fingers can be force-guided back to the open position at a controlled rate. If the digits are engaged by the electromagnetic actuation mechanism while the motor is static and the pawls are released, the digits will remain in the same position. The digits can be digitized using an electronic control scheme to gradually release and stop the digits by engaging and disengaging the electromagnetics as needed until the desired digit positions are achieved. If all digits or one finger is engaged by the mechanism, the motor can be reversed to force-drive the digits back to the open position. However, in this configuration, constraints on the mechanism would prevent digitized fingers from being able to engage and disengage separately. Digits can also be engaged or disengaged separately from the electromagnets and the rotating shaft as the motor turns backwards to achieve the desired hand or grasping movements. Moreover, to produce flexion and releasing movements in the same hand movement, specific control algorithms than can be written using known languages and methods in the art can be used to digitize the desired digits forwards and backwards.

Digitizing, or power sharing, with the digits is the ability of the mechanism to distribute different power levels to different digits at any moment. Digitizing is quantified as the on and off engagement or disengagement of the electromagnetic actuation system or motor and the clicking of the pawl/ratchet gear as the digits are manipulated to perform a grasping function. The grasping of the hand or digits can be quantized by the time of electromagnetic engagement and the pawl/ratchet clicks needed to achieve a grasp, where a pawl click is equal to $1/n^{th}$ of the ratchet rotation, wherein n is the number of teeth on the ratchet gear included in the full range of motion of each digit. The control logic and software that can be used in order to digitize the digits is known to those skilled in the art.

In the preferred additional embodiment that uses digitization, five digits are connected to one rotating shaft, and the digits are engaged by the electromagnetic actuation and manipulated as needed. Digitizing is accomplished by being able to engage or disengage any digits from the spinning shaft at any given instance via the electromagnetic actuation system, and, when engaged, the ability to distribute various power levels as needed per grasp or slippage correction (the gears will incrementally be clicked until the desired digit force is achieved). The speed of the shaft and digit engagement to the shaft can be chosen per application and to the wearer's preference.

The noise of the device is greatly reduced, compared to known devices, due to one motor being used to provide flexion to all digits. A majority of the prosthetic hands known in the art have an individual high rotations-per-minute, gear reduced motor per digit which accumulates to several motors per hand. When in use, regardless of the necessary movement needed, these motors contribute to high noise levels. The disclosed mechanism only uses one high torque, low rotations-per-minute motor for flexion of all five digits. The mechanism can also include or exclude a gearbox. This greatly reduces both the noise level and power consumption of the prosthetic hand. The sounds of the mechanism, clicking pawls, clicking electromagnets, spinning belt, and revving motor is naturally quieter with one motor versus the six motors used in known devices. Further, the quickness of this device makes any noise produced brief and far more unnoticeable. Moreover, the nature of noises produced is short duration burst of low energy, high frequency noise that can be absorbed and masked creatively compared to multi-gear noises. This is an important consideration for prosthetic hand users because noise draws unwanted attention to the users, which puts their handicap in the forefront of any social interactions.

Another benefit of this novel design is reduced battery consumption of the mechanism due to several factors including the locking mechanism, spring release system, and lack of actuators as compared to other hands. Due to the use of only one motor 20 and one shaft for flexion of all of the digits, individual locking mechanism (motor does not need to be engaged to lock in the grasping position), spring released digits (motor is not needed to bring the fingers back to the open position), the mechanism has a reduced battery power consumption compared to other hands that have multiple motors for digit flexion. Moreover, due to the quickness of this mechanism, the motor and the electromagnets are very briefly engaged for fractions of a second to complete a grasp. Other hands have to "rev-up" and down the motors to complete a grasp leading to more battery power consumption and more noise.

Additionally, the digitizing and locking of the digits allows for digits to grasp and hold heavier objects as opposed to existing prosthetic hands. Being that the pawl locking mechanism locks the digits in place, the loads are taken off of the electromagnetic engagement system and placed solely on the pawls during a static grip. This allows for greater loads to be held and prevents any damage to the mechanism. With that said, the "slip clutch" design of the magnetic actuation system also prevents damage to the entire mechanism when overbearing loads are attempted. The friction engagement mechanism between the ratchet gear and the spline nut assembly (or the ERSC assembly as disclosed in alternative embodiments) is specifically designed to slip at a certain load, preventing any damage to the prosthetic unit. Moreover, the digitizing ability allows for extra power to be placed where it is needed as an object is being grasped, dynamically held, or when slippage occurs. This is a benefit of the "power-sharing" feature of this design wherein the entire power of the motor can be dedicated to one digit or any combination of digits depending on where power is needed.

Due to the quickness and speed of the mechanism—less than 1 full turn of the drive shaft is needed to completely close a digit—once a command signal is received from the user, the mechanism quickly engages the motor 20, the electromagnet engages the ratchet gears 4 and then spins the shaft 13 to complete a grasp ("Short Duty Cycle"). Depending on the selected gear ratios and user preferences, the mechanism can be geared to close all fingers with less than one turn of the shaft. Incremental pawl clicks and force feedback on each digit is independent of motor torque and speed changes due to the electromagnetic engagement system not always being engaged. There is no need to wait for the miniature micro motor used in other hands to rev-up or down to spin enough times to complete a grasping movement. So, from signal acquisition to completing a grasp, the dynamics of the mechanism allow it to be quicker and stronger than other hand mechanisms.

The quick actuation attribute and other advantages of the driving mechanism of the hand make the system a good candidate to interface with existing and future control strategies and technologies based around the prosthetic industry. Those persons skilled in the art will recognize that known control logic can be implemented with this novel prosthetic hand device. Due to the multiple dynamics of the mechanisms, especially its ability to quickly engage and disengage between multiple actions and movements simultaneously allows for more complex control schemes to be implemented with the mechanism. More sophisticated logic and control strategies have the possibility to increase the functionality of the hand and allow it to make other advancements not capable with hands currently known in the art, as well as additional future embodiments. For example, calibration constants can be stored, compared, and adjusted to compensate for wear, aging over time, and for performance enhancements by the microprocessors during idle decision cycles between commands. Current hand technologies lack these capabilities due to the lack of functionality and the bulkiness of the current designs.

An additional benefit of this new device is the implementation of individual digits which allows for affordable replacements. The mechanism is set up to be used as a modular design. Each digit is considered a unit in itself. Each digit system consists of a ratchet gear 4 and pawl 12, a magnetic actuation system, a spline nut assembly 36, a proximal phalange 33, intermediate phalange 27, and distal phalange 28 along with a finger cable 3. Moreover, hand attributes like wear and tear on the internal components can be tracked and alerted to users in the form of a maintenance report. In later developments of the design, reports can alert users of minor repairs that are needed before costly failures occur. These units are intended to be replaceable and fixable by replacing the individual digit unit instead of the entire device.

In an additional embodiment, an additional motor 20 is included in the device to control thumb rotation. This design still provides many of the benefits as disclosed previously because this configuration uses only one motor to provide individual flexion of the digits and thumb and one motor to control thumb rotation. In the current art, six motors are required to provide similar functionality.

In an additional embodiment, an electromagnetic rotary solenoid clutch ("ERSC") with a ratchet gear can be used as part of the magnetic actuation. This design is constructed using a combination of a rotary solenoid and an electromagnetic clutch. The unique clutch design allows for a splined nut attached to the spline shaft to rotate inside of the clutch's hollow magnetic steel core while providing axial motion to the spline but by use of electromagnetic force. The ERSC is a separate entity of the shaft and allows for multiple ERSC's to be used on single shafts.

An additional innovative aspect of the ERSC assembly 10 is that it transmits motion to the digits from the shaft by mimicking a friction drive transmission system. Friction drive is a mechanical principle that utilizes friction force to transmit torque and power. A friction drive transmission is utilized by mounting the plunger assembly 7 perpendicularly to the face of the rubber washer 6. The use of a friction drive transmission, which has not previously be utilized in prosthetic hands, allows for slippage to occur between the two contacting surfaces when loads above the mechanism's threshold dynamic load are grasped. This configuration prevents possible damage to the mechanism's hardware. Additionally, the use of a friction drive to engage and disengage finger movement allows for the quick engagement and disengagement of finger actuation, which in turn allows for hand movements to be performed quickly and without hesitation.

While the disclosed apparatus was designed for use in medical prosthetic hands, the features and advantages of this design described in this application can be utilized by a number of different industries including but not limited to the automotive, automation, agricultural, and construction fields. In an additional embodiment, this hand could be used in robotics applications in which the flexion and dexterity of a human hand is needed to perform the particular task.

The described features, advantages, and characteristics may be combined in any suitable manner in one or more embodiments. One skilled in the relevant art will recognize that the various components of this design may be practiced without one or more of the specific features or advantages of a particular embodiment. In other instances, additional features and advantages may be recognized in certain embodiments that may not be present in all embodiments.

I claim:

1. An apparatus designed for use as a prosthetic or artificial hand comprising:
   at least one locking mechanism;
   an electromagnetic actuation system;
   a spline nut and shaft assembly;
   a timing belt;
   a spline shaft pulley;
   a motor; and
   a hand configuration.

2. The apparatus of claim 1, wherein the locking mechanism comprises:
   at least one ratchet gear;
   at least one pawl; and
   a one-way bearing.

3. The apparatus of claim 2, wherein the ratchet gears are located on the spline shaft with the spline nut and shaft assembly.

4. The apparatus of claim 2, wherein the pawls and one-way bearing are located on the pawl train shaft, which is parallel to the spline shaft.

5. The apparatus of claim 2, wherein the pawls are driven by the timing belt which is operated directionally through the one-way bearing.

6. The apparatus of claim 2, wherein, during operation, the spline shaft spins with the ratchet gears, causing the pawl to ratchet on top of the ratchet gear until the spline shaft stops spinning.

7. The apparatus of claim 1, wherein the electromagnetic actuation system comprises:
   at least two pusher plates;
   at least two electromagnetic coil cores;
   at least two electromagnetic coils; and
   at least four magnetic poles;
   wherein the electromagnetic coils are wrapped around the electromagnetic coil core;
   wherein a magnetic pole is located at each end of the electromagnetic coil core combination.

8. The apparatus of claim 1, wherein the hand configuration comprises:
   at least one digit unit; and
   a mechanism platform.

9. The apparatus of claim 8, wherein each of the digit units is spring-loaded.

10. The apparatus of claim 9, wherein each of the digit units is spring-loaded with dampening springs.

11. The apparatus of claim 8, wherein each of the digit units comprises:
    a proximal phalange;
    an intermediate phalange;
    a distal phalange;
    a finger rod;
    a spring; and
    a finger cable;
    wherein the finger cable engages with the ratchet and pawl system to operate the fingers; and
    wherein the proximal phalange and intermediate phalange are connected by the finger rod.

12. The apparatus of claim 8, wherein each of the digit units further comprises a distal phalange.

13. The apparatus of claim 8, wherein each of the digit units comprises a locking mechanism.

14. The apparatus of claim 8, wherein the digit units are further operated using an electronic control scheme to gradually release and stop digit movement.

15. The apparatus of claim 1, wherein a friction engagement mechanism is designed to slip at a designated load.

16. The apparatus of claim 1 further comprising a second motor.

17. An apparatus designed for use as a prosthetic or artificial hand comprising:
    a locking mechanism;
    at least one electromagnetic actuation system;
    a spline nut and shaft configuration;
    a timing belt;
    a spline shaft pulley;
    a motor;
    a gear micro-motor; and
    a hand configuration;
    wherein the ratchet gears are located on the spline shaft with the spline nut and shaft assembly;
    wherein the pawls and one-way bearing are located on the pawl train shaft, which is parallel to the spline shaft;
    wherein the pawls are driven by the timing belt which is operated directionally through the one-way bearing;
    wherein, during operation, the spline shaft spins with the ratchet gears, causing the pawl to ratchet on top of the ratchet gear until the spline shaft stops spinning;
    wherein the hand configuration is comprised at least two individual finger mechanisms;
    wherein the electromagnetic actuation system is comprised of an electromagnetic rotary solenoid clutch configuration, comprised of a rotary solenoid and an electromagnetic clutch, wherein a splined nut attached to the spline shaft rotates inside of the clutch's hollow magnetic steel core while providing horizontal motion through electric forces; and
    wherein the motor is used to drive all of the finger mechanisms on the apparatus.

18. The apparatus of claim 17 wherein the electromagnetic clutch is comprised of a spline nut and a rubber washer, wherein the rubber washer and spline nut are perpendicularly placed.

19. The apparatus of claim 17 wherein the electromagnetic rotary solenoid clutch configuration is comprised of:
    a plunger assembly comprising:
        a spline nut;
        a flanged T-nut; and
        ball bearings;
    an inner steel core;
    at least two washers;
    wire; and
    an outer coil casing;
    wherein the wire is wrapped around the inner steel core.

20. The apparatus of claim 17, wherein the hand configuration is controlled by the at least one individual electromagnetic rotary solenoid clutch configuration.

21. The apparatus of claim 17 wherein the finger mechanisms are spring-loaded with dampening springs.

22. The apparatus of claim 17 wherein the friction engagement mechanism is designed to slip at a designated load.

23. The apparatus of claim 17 further comprising an additional motor wherein said additional motor is configured to control thumb rotation.

\* \* \* \* \*